(12) United States Patent
Jodaikin et al.

(10) Patent No.: US 9,668,844 B2
(45) Date of Patent: Jun. 6, 2017

(54) DEVICE FOR FIXATION AT A DENTAL SITE

(71) Applicant: Colldent Y.A. Ltd., Kiryat Yearim (IL)

(72) Inventors: Aharon Jodaikin, Judean Hills (IL); Hilary Jodaikin, Judean Hills (IL)

(73) Assignee: COLLDENT Y.A LTD, Kiryat Yearim (IL)

( * ) Notice: Subject to any disclaimer, the term of this patent is extended or adjusted under 35 U.S.C. 154(b) by 163 days.

(21) Appl. No.: 14/073,506

(22) Filed: Nov. 6, 2013

(65) Prior Publication Data

US 2015/0125810 A1 May 7, 2015

(51) Int. Cl.
*A61C 7/00* (2006.01)
*A61C 19/06* (2006.01)
(Continued)

(52) U.S. Cl.
CPC .......... *A61C 19/066* (2013.01); *A61C 19/063* (2013.01); *A61K 8/0208* (2013.01);
(Continued)

(58) Field of Classification Search
CPC ..... A61C 19/063; A61C 5/127; A61C 19/066; A61Q 11/00; A61K 8/0208; A61K 2800/87; Y10T 29/49567
See application file for complete search history.

(56) References Cited

U.S. PATENT DOCUMENTS 2,835,628 A 5/1958 Saffir
3,679,360 A 7/1972 Bernard et al.
(Continued)

FOREIGN PATENT DOCUMENTS

DE 202006003819 6/2006
EP 0389224 9/1990
(Continued)

OTHER PUBLICATIONS

A guide to the use of fluorides for the prevention of dental caries, A JADA Publication, vol. 113, pp. 504-564, 1986.
(Continued)

*Primary Examiner* — Heidi M Eide
(74) *Attorney, Agent, or Firm* — Dorsey & Whitney LLP

(57) ABSTRACT

A reshapable retention device for insertion at a dental site and contact with adjacent dental surfaces, for the controlled delivery to the dental site of at least one material having a predetermined intraoral activity. The retention device comprises at least one matrix containing the material. The retention device is adapted for physically affixing at the dental site for at least a predetermined time period correlated to the delivery of a predetermined portion of the at least one matrix to the dental site in a controlled single, bi or multi-phase pattern. The retention device comprises a first configuration in which the overall dimensions of the retention device are larger than at least one dimension of the dental site. The first configuration is reshapable to a second configuration in which at least one dimension of the retention device is reduced to enable physically affixing the retention device at the dental site. In the second configuration the retention device comprises a predetermined shape having contours for affixing at the dental surfaces.

16 Claims, 21 Drawing Sheets

(51) Int. Cl.
*A61Q 11/00* (2006.01)
*A61K 8/02* (2006.01)
*A61C 5/12* (2006.01)

(52) U.S. Cl.
CPC .............. *A61Q 11/00* (2013.01); *A61C 5/127* (2013.01); *A61K 2800/87* (2013.01); *Y10T 29/49567* (2015.01)

(56) References Cited

U.S. PATENT DOCUMENTS

| | | | |
|---|---|---|---|
| 3,754,332 | A | 8/1973 | Warren, Jr. |
| 3,851,972 | A | 12/1974 | Smith et al. |
| 3,900,290 | A | 8/1975 | Hornstra |
| 3,923,939 | A | 12/1975 | Baker et al. |
| 4,556,561 | A | 12/1985 | Brown et al. |
| 4,576,190 | A | 3/1986 | Youssef |
| 4,638,823 | A | 1/1987 | Newman et al. |
| 4,685,883 | A | 8/1987 | Jernberg |
| 4,741,700 | A | 5/1988 | Barabe |
| 4,772,325 | A | 9/1988 | Kwan et al. |
| 4,837,007 | A | 6/1989 | Duckworth et al. |
| 4,892,483 | A | 1/1990 | Douglas, Jr. |
| 4,892,736 | A | 1/1990 | Goodson |
| 4,923,683 | A | 5/1990 | Sakuma et al. |
| 4,938,763 | A | 7/1990 | Dunn et al. |
| 4,983,334 | A * | 1/1991 | Adell .................... A61C 13/04 264/138 |
| 5,074,786 | A | 12/1991 | Woodward |
| 5,077,049 | A | 12/1991 | Dunn et al. |
| 5,197,882 | A | 3/1993 | Jernberg |
| 5,278,201 | A | 1/1994 | Dunn et al. |
| 5,324,519 | A | 6/1994 | Dunn et al. |
| 5,373,599 | A | 12/1994 | Lemon et al. |
| 5,460,803 | A | 10/1995 | Tung |
| 5,579,786 | A | 12/1996 | Wolk et al. |
| 5,605,677 | A | 2/1997 | Schumann et al. |
| 5,639,840 | A | 6/1997 | Fife et al. |
| 5,733,950 | A | 3/1998 | Dunn et al. |
| 5,739,176 | A | 4/1998 | Dunn et al. |
| 5,770,182 | A | 6/1998 | Fischer |
| 5,840,329 | A | 11/1998 | Bai |
| 5,869,096 | A | 2/1999 | Barclay et al. |
| 5,875,799 | A | 3/1999 | Petrus |
| 5,998,431 | A | 12/1999 | Tseng et al. |
| 6,068,859 | A | 5/2000 | Curatolo et al. |
| 6,106,811 | A | 8/2000 | Gibbs |
| 6,136,297 | A | 10/2000 | Sagel et al. |
| 6,183,775 | B1 | 2/2001 | Ventouras |
| 6,200,136 | B1 * | 3/2001 | Prasad .................... A61C 5/00 433/180 |
| 6,287,120 | B1 | 9/2001 | Wiesel |
| 6,343,932 | B1 | 2/2002 | Wiesel |
| 6,521,215 | B2 | 2/2003 | Okay |
| 6,565,960 | B2 | 5/2003 | Koob et al. |
| 7,118,376 | B2 | 10/2006 | Jodaikin et al. |
| 2003/0006828 | A1 | 1/2003 | Kohsiek |
| 2003/0068284 | A1 | 4/2003 | Sagel et al. |
| 2005/0017595 | A1 | 1/2005 | Strobl |
| 2005/0100853 | A1 * | 5/2005 | Tadros ................ A61C 19/063 433/6 |
| 2005/0175959 | A1 | 8/2005 | Jodaikin et al. |
| 2009/0042161 | A1 * | 2/2009 | Jodaikin .............. A61C 19/063 433/80 |
| 2012/0028219 | A1 * | 2/2012 | Emerton .............. A61C 19/063 433/180 |

FOREIGN PATENT DOCUMENTS

| | | |
|---|---|---|
| JP | 2001163768 | 6/2001 |
| WO | WO-9816503 | 5/1998 |
| WO | WO-0168038 | 9/2001 |

OTHER PUBLICATIONS

Addadi et al, Stereochemical aspects of crystal regulation in calsium phosphate-associated mineralized tissues, Chemistry and Biology of Mineralized Tissues, pp. 153-162, 1992.
Addadi et al., Control and Design Priniciples in Biological Mineralization, Angew. Chem. Int. Ed. Engl. vol. 31, pp. 153-169, 1992.
Addadi et al., Macromolecole-Crystal Recognition in Biomineralization, American Chemial Society, No. 444, pp. 13-27, 1991.
Bailey et al., Identification of two interchain crosslinks of bone and dentine colagen, Biochem and Biophys. Research Communications, vol. 35, pp. 663-671, 1969.
Berry et al., Amalgram at the New Millennium, JADA, vol. 129, pp. 1547-1556, 1998.
Bourges et al., General Properties of Silated Hydroxyethylcellulose for Potential biomedical Applications, Biopolymers, vol. 63, pp. 232-238, 2002.
Bourges et al., Synthesis and gerneral properties of silated-hydroxypropyl methylcellulose in prospect of biomedical use, Advances in Colloid and Interface Science, vol. 99, pp. 215-228, 2002.
Caufield, The Biological Basis of Dental Caries, Harper and Row Publishers, pp. 406-407, 1980.
Clarkson et al., Phosphoprotein Analysis of sequential Extracts of Human Dentin and the determination of the Subsequent Remineralization Potential of these Dentin Matrices, Caries Research, vol. 32, pp. 357, 1998.
Clarkson et al., SEM and Microprobe Analyses of Enamel-metal-fluoride Interactions, Journal of Dental Research, vol. 60, pp. 1912-1920, 1981.
Craig et al., Dental Materials, Properties and Manipulation, The C. V. Mosby Company, pp. 2-28, 1979.
Cury et al, Effect of a calcium carbonate-Based Dentifrice on Enamel Demineralization in situ, Caries Research, vol. 37, pp. 194-199, 2003.
Davis et al., The Effects of Benzoate and fluoride on Dental Caries in Intact and Desalivated Rats, Caries Research, vol. 35, pp. 331-337, 2001.
Donly et al., Evaluating the effects of Fluoride Releasing Central Materials on Adjacent Interporximal Caries, JADA, vol. 130, pp. 817-825, 1999.
Exterkate et al., A Single-section Model for Enamel Do- and Remineralization Studies, J Dent Res, vol. 72, pp. 1599-1603, 1993.
Glickman, Clinical Periodoutology, W. B. Saunders Company, pp. 18-19, 1972.
Guo et al., Comparison of Fluoride Uptake Produced by Tray and Flossing Methods in vitro, J. Dent. Res. vol. 68, pp. 496-498, 1989.
Harris et al., Primary Preventive Dentistry 4th Edition, Norwalk Appleton Longe 1995.
Hoffman et al., Histopathology of Caries Lesions, Harper & Row, pp. 226-246, 1980.
Hormann et al., Metal Ions in Biological Systems, New York Marcel and Dekker, vol. 3 , p. 105, 1974.
Inaba et al., Effect of Sodium Hypochlorite Treatment on Remineralization of Human root dentine in vitro, Caries Research, vol. 30, pp. 218-224 1996.
Jenkins, G. Neil, The Physiology and Biochemistry of the Mouth, Blackwell Scientific Publishing, p. 495, 1978.
Jodaikin et al., Possible products at tooth-amalgam interfaces, J. Dent., vol. 16, pp. 140-144, 1988.
Kautsky et al., Effect of Salivary Components on Dissolution Rates of Carbonated Apatites, Caries Res., vol. 27, pp. 373-377, 1993.
Kay, L.W., Drugs in Dentistry, Bristol, John Wright & Sons Ltd, pp. 242-243, 1972.
Kodaka et al., Hexahedrallly Based Crystals in Human tooth Enamel, Caries Research, vol. 26, pp. 69-76, 1992.
Kopel et al., The effects of glutaraldehyde on primary pulp tissue following coronal amputation: an in vivo histologic study, Journal of Dentisry for Children, vol. 47, pp. 425-430, 1980.
Koulourides, T., Art and Science of Dental Caries Research, pp. 355-378,1968.

(56) References Cited

OTHER PUBLICATIONS

Legler et al., Definition, Etiology, Epidemiology and Clinical Implications of Dental Carries, Menacker, Harper & Row, pp. 211-225, 1980.
Levi-Kalisman et al., X-Ray absorption spectrosopy studies on the structure of a biogenic "amorphous" calcium carbonate phase, J. Chem Soc. Dalton Trans, pp. 3977-3982, 2000.
Loty et al., In vitro bone formation on a bone-like apatite layer prepared by a biomimetic process on a bioactive glass-ceramic, J. Biomed Mater Research,vol. 49, pp. 423-434, abstract 2000.
Magazine of Dental Association, Research on Teeth Separation Rubber with Fluorine Sustained-Release Property, item 74, vol. 52, No. 11, p. 134, 2000.
Mandel, Irwin D., Changing patterns of dental caries, Quinlessence International, vol. 16, pp. 81-87, 1985.
Massler, M., Preventive Endodontics: Vital Pulp Therapy, Dental Clincis of North America, pp. 663-673, 1967.
Miller et al., Lasers in Dentistry: An Overview, JADA, vol. 124, p. 32, 1993.
Mjor, I.A., Alternative Surgical Techniques in Operative Dentistry, Quintessence Int., vol. 29, pp. 600-602, 1998.
Nathanson et al. "In Vitro Elution of Leachable Components form Dental Sealants", JADA, vol. 128, pp. 1517-1523, 1997.
O'Brien et al., An Outline of Dental Materials and their selection, W.B. Saunders Company, p. 127, 1978.
Orban et al., Crooslinking of collagen gels by transglutaminase, J of Biomedical Materials Research, vol. 68A, pp. 756-762, 2004.
Ostrom, C.A., Fluorides in Dentistry, Harper & Row, pp. 445-460, 1980.
Paine,et al., Floride use in Periodontal Therapy: A Review of the Literature, JADA vol. 129, pp. 69-77, 1998.
Pearce et al., Remineralization of Softened bovine Enamel following Treatment of Overlying Plaque with a Mineral-enriching Solution, J. Dent Research, vol. 64(3), pp. 416-421, 1985.
Poole et al., Remineralization of enamel, Elsevier Scientific Pub. Co., pp. 35-56, 1973.
Rawls, H.R., Preventive Dental Materials: Sustained Delivery of Fluoride and Other Therapeutic Agents, Adv. Dent. Res., vol. 5, pp. 50-55, 1991.
Rose et al., Fluoride Depsition on Interproximal Tooth Surfaces by a Wedge Treatment, J. Dent. Res., vol. 77, p. 972, 1998.
Saxe et al., Alzheimer's Disease Dental Amalgam and Mercury, JADA, vol. 130, pp. 191-199, 1999.
Shellis et al, Organic material and the optical properties of the dark zone in caries lesions of enamel, European Journal of Oral Sciences, vol. 110, pp. 392-395, 2002.
Soderholm et al., BIS-GMA-Based Resins in Dentistry: Are they safe?, JADA, vol. 130, pp. 201-209, 1999.
Steinberg et al., Despendable contained release device for local treatment of periodontal diseases, J. Dent. Res. pp. 67-208 Abstract No. 767, 1988.
Takagi et al., Effect of Tooth-Bound Fluoride on Enamel Demineralization/Remineralization in vitro, Caries Res., vol. 34, pp. 281-288, 2000.
Takatsuka, T., Enamel remineralization by Isomalt toothpaste in situ, J. Dent Res. 81 (Sp Iss. A), #2815, 2002.
Tanaka et al., Acid resistance of human enamel in vitro after bicarbonate application during remineralization, Journal of Dentistry, vol. 29, pp. 421-426, 2001.
Traub et al., A. Adv. Protein Chem., vol. 25, pp. 243-352, 1971.
Turezyn et al., In situ self-hardening bioactive composite for bone and dental surgery, J. Biomater Sci. Polym Ed, vol. 11, pp. 217-223, 2000.
Vandelli et al., Microwave-treated gelatin microspheres as drug delivery system, Journal of controlled release, vol. 96, pp. 67-84, 2004.
Wefel et al., De/remineralization from sodium fluoride dentifrices, Am. J. Dent., vol. 8, pp. 217-220, 1995.
Wefel et al., The Use of Saturated DCPD in Remineralization of Artificial Caries Lesions in vitro, Journal of Dental Research, vol. 66, pp. 1640-1643, 1987.
Winston et al., Caries Prevention in the 21st Century, JADA, vol. 129, pp. 1579-1587, 1998.
Wu et al., A study of the mechanism of effects of solution containing trace elements on remineralization layer formation of enamel carious lesions, National Library of Medicine, vol. 18, pp. 219-221, 2000.
Zhang et al., The Improved Remineralization and Fluoride Uptake in Vivo of Triclosan/Copolymer/Sodium Fluoride Toothpasic vs. Sodium Fluoride Toothpaste, J. Clin. Dent, vol. 14, pp. 23-28, 2003.
Zimmerman et al., Prevention of in vitro Secondary Caries with an Experimental Fluoride-exchanging Restorative Resin, J. Dent. Res., vol. 63, pp. 689-692, 1984.
U.S. Appl. No. 13/652,242, filed Oct. 15, 2012.

\* cited by examiner

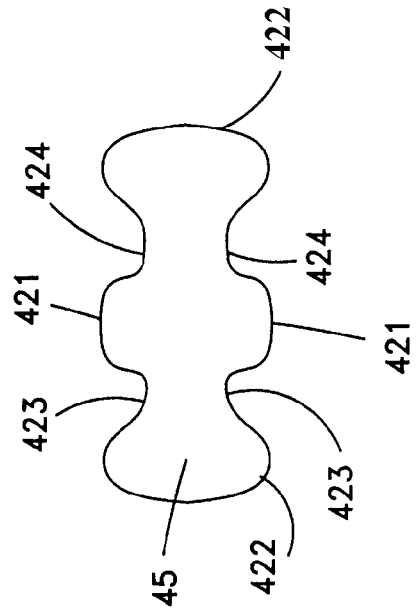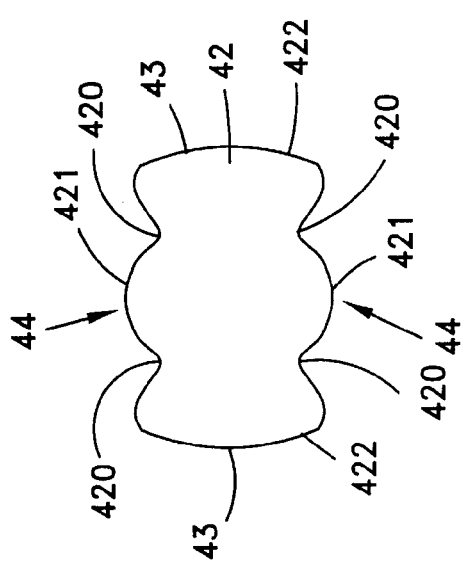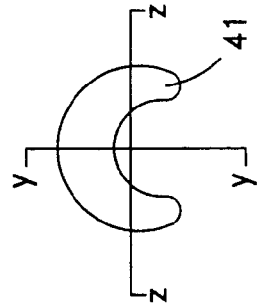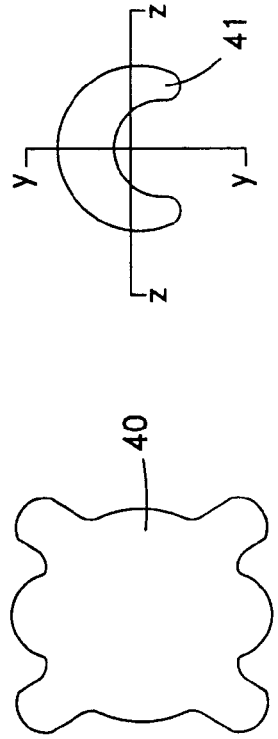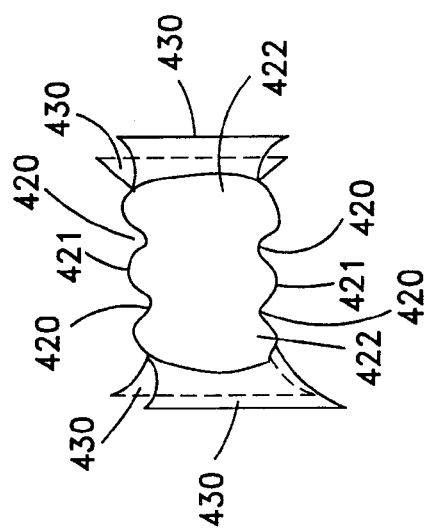

Section xx-xx

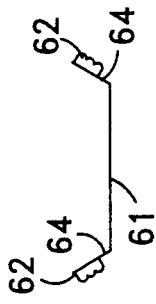
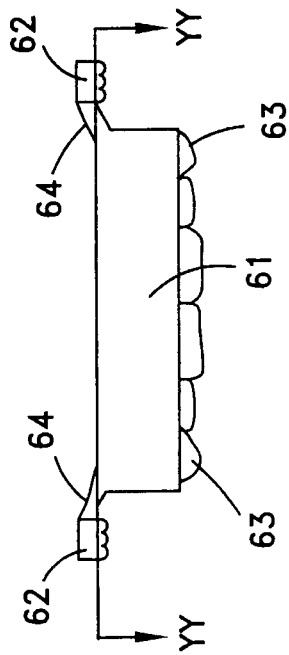
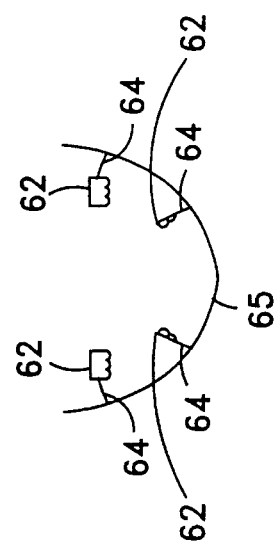
Fig. 6(a)
Fig. 6(b)
Fig. 6(c)

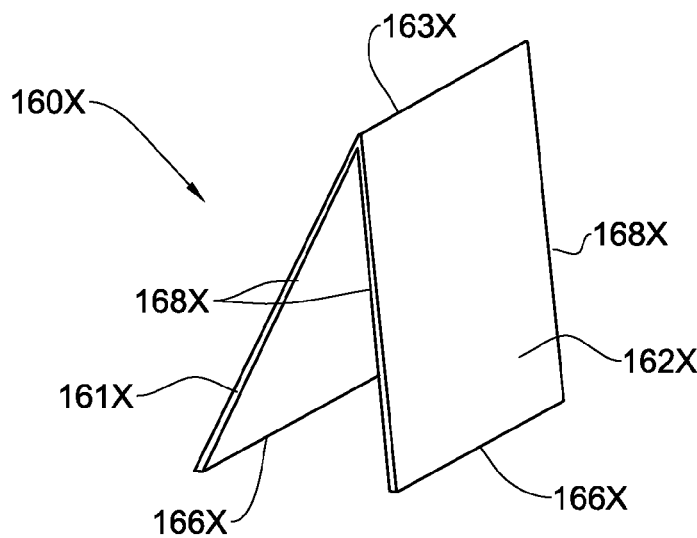
Fig. 16(a)
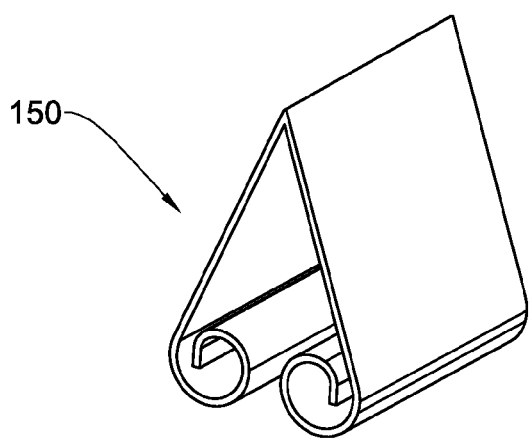
Fig. 16(b)
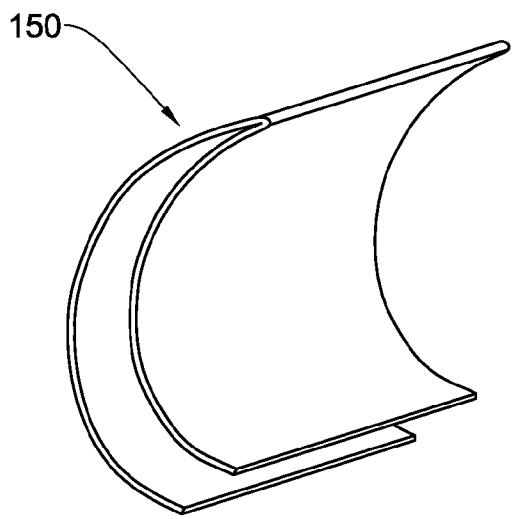 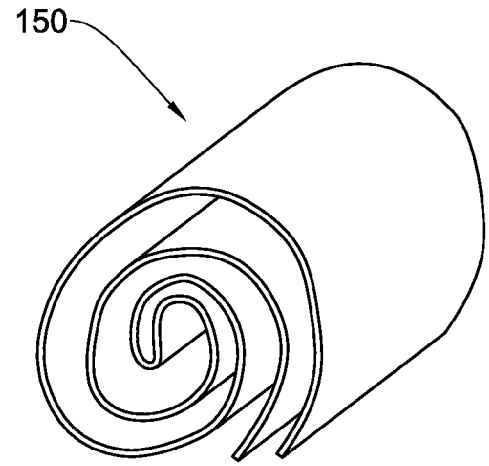
Fig. 16(c)              Fig. 16(d)

DEVICE FOR FIXATION AT A DENTAL SITE

FIELD OF THE INVENTION

The present invention relates generally to oral devices.

BACKGROUND OF THE INVENTION

A significant percentage of dental caries (demineralization, decay) occurs between teeth (interproximally, aproximally). This difficult, inaccessible region has been recognized as a problem for more than half a century. Approaches have ranged from grinding of the interproximal surfaces to make them self-cleansing and thus caries "immune" (Mjor, I. A. Quintessence Int. 29: 600-602, 1998) to flossing between the teeth which requires fastidious patient compliance and smooth surfaces. The inclusion of fluoride (U.S. Pat. No. 4,638,823) and other agents in dental floss (U.S. Pat. No. 5,875,799) and other electric (U.S. Pat. No. 5,579,786) or mechanical and chemical devices (U.S. Pat. Nos. 4,576,190, 4,638,823 and 5,373,599) does not appear to have significantly reduced interproximal caries. There is thus, a need to develop a technique or device which overcomes these limitations and the disadvantages of flossing between the teeth.

Various means of chemically preventing or treating such lesions, as well as other problems such as discoloration and sensitivity are described by the inventors of the present invention in U.S. Pat. No. 7,118,376 and its co-pending US Continuation In Part Application, Publication No. 2005-0175959, the contents of which, including publications referenced therein, is fully incorporated herein by reference.

In U.S. Pat. No. 7,118,376 the inventors of the present invention, describe a system for the controlled delivery of at least one material having a predetermined intraoral activity to an interproximal site of at least one dental surface in an oral cavity. The system comprises a polymeric matrix containing the said material. The system is sufficiently flexible for insertion at the interproximal site to be physically affixed thereat and sufficiently tough to maintain mechanical integrity at the interproximal site for the required amount of time and for a predetermined amount of time. The interproximal site is defined in U.S. Pat. No. 7,118,376 as an area of contact and surrounding surfaces between the dental surface and an adjacent dental surface. The co-pending US Continuation In Part Application, Publication No. 2005-0175959, discloses the delivery of a predetermined portion of the at least one matrix to the interproximal site in a controlled single, bi or multiphase pattern.

However, the system described in U.S. Pat. No. 7,118,376 and its co-pending US Continuation In Part Application, Publication No. 2005-0175959 is not directed to gingival and periodontal disease, or to the general systemic treatment or prevention related to the oral cavity and digestive system. Moreover, they do not relate to subtle anatomic nuances of the dentition and gingival and periodontal tissue in healthy or pathologic states.

The restoration of interproximal cavities, for example dental filling procedures, requires packed filling material to be retained in position in a tooth for a period of time. A thin flexible strip made of metal, plastic or other suitable material, known as a dental matrix band (or band, or matrix) is typically wrapped around the sides of the tooth being restored to maintain the filling in place while and after the filing has been placed to prevent the filling from distorting or flowing out of the desired tooth contour. Thus, a matrix band acts as a template to facilitate reestablishment of lost tooth contour by the filling material. A small wedge is often used, lodged in the interproximal space between the band and adjacent tooth to urge the band into close contact with the tooth being restored, and thus ensure that the band is held properly in place. A retention device that is fine tuned to anatomical nuances of the interproximal site and that limits and avoids the need for a wedge will facilitate proper placement of the matrix band at the interproximal site without encroaching on and/or causing damage to the gingiva or at least limiting such damage. Moreover, a retention device that itself acts as a template to facilitate reestablishment of lost tooth contour by the filling material may minimize costs involved with such procedures by reducing the amount of time and maximizing efficiency of the procedure.

It is therefore an object of the present invention to provide a retention device for physically affixing at a dental site.

At least one example of the present invention provides a reshapable device for physically affixing at a dental site to have a desired or predetermined activity to at least one desired dental surface in the oral cavity, or into the oral cavity, which overcomes the disadvantages of the prior art.

At least one example of the present invention provides such a device that is particularly directed to the anatomical areas of interproximal sites and furcations.

At least one example of the present invention provides a system for fixing a plurality of devices intraorally.

At least one example of the present invention provides such a device that is partially or fully configured according to the contours of dental and soft tissue surfaces.

At least one example of the present invention provides such a device that employs at least one matrix as a carrier for active material.

At least one example of the present invention provides such a device in which the matrix for the active material may be biodegradable, resorbable or non-resorbable.

At least one example of the present invention provides such a device which is particularly adapted for physical fixation at a dental site, for at least a predetermined time period, typically sufficient to enable the controlled or sustained delivery of a required quantity of the active material from the matrix or matrices to the surfaces and/or oral cavity.

At least one example of the present invention provides such a device in which the physical affixing of the device is by way of a physical property of the matrix, in particular wherein the matrix comprises a hydrophilic polymer which softens and swells in situ by the hydration thereof in the oral cavity after accommodation at the dental site.

At least one example of the present invention provides such a device which is adapted on the one hand to accommodate the matrix and align the same with the dental site, and on the other hand is also adapted for affixing at the site by virtue of its shape, configuration and elasticity/resilience of the material from which it is made. In particular, such adaptation includes sufficient elasticity and toughness of the matrix material, which are important criteria when positioning the matrix between teeth.

At least one example of the present invention provides such a system wherein the device is sufficiently flexible for insertion into an interproximal site, and at the same time of sufficient toughness to maintain mechanical integrity thereat, while being soft enough not to be a source of discomfort within the oral cavity prior to its removal or biodegration.

At least one example of the present invention provides any one or combination of a plurality of chemical and other agents that have a desired activity at the dental site, in particular such as to enable inter alia the cleaning, prevention, treatment, diagnosis, cosmetic treatment (whitening/bleaching and mouth/breath freshening), elimination or retardation of dental caries at tooth surfaces or at tooth interfaces with restorations or prostheses or to treat gingival or periodontal disease.

At least one example of the present invention provides a system that is shaped to fit over a portion of, or an entire single dental arch.

At least one example of the present invention provides such a device that is designed to release a chemical agent into the saliva for a desired or predetermined activity therewithin or in the digestive tract or absorption into the body.

At least one example of the present invention provides such a device which includes at least one adhering agent.

At least one example of the present invention provides such a device in a specific, controlled micro-environment which selectively excludes at least one element or molecule present in the mouth by way of a physical or chemical property of the matrix or matrices.

At least one example of the present invention provides such a device in a specific, controlled micro-environment which optimizes the delivery of a least one element, molecule or agent to the said dental site. The said element, molecule or agent can be exogenous, from the device, or endogenous, e.g. directly or indirectly from the saliva.

At least one example of the present invention provides such a system that employs at least one matrix to deliver a single phase controlled release pattern or a bi- or multiphase controlled release pattern to deliver at least one agent at an appropriate or optimal time, stage, manner or form.

At least one example of the present invention provides such a system that employs at least one bi- or multi-layer or bi- or multi-located matrix to provide a single phase, biphase or multiphase controlled release system.

At least one example of the present invention provides such a system that employs at least one matrix which keeps the active material or materials inactive by chemical means such as inhibition or physical separation in order to allow at least one agent to be delivered at an appropriate or optimal time, stage, manner or form.

In at least one example of the present invention the device is adapted to facilitate affixing at least one matrix band at the interproximal site to restore at least one cavity.

In at least one example of the present invention the device itself is adapted physically or chemically to allow the restoration of at least one interproximal cavity.

Additional features of at least some examples of the present invention will become apparent as the description proceeds.

SUMMARY

Thus, according to certain aspects, the present invention provides a method for the prevention and/or treatment of dental caries in a patient in need thereof, comprising applying at a dental site of said patient the matrix or matrices according to the invention, wherein the material is at least one fluoridation agent, and/or at least one remineralization agent, and/or at least one mineralization agent, and/or at least one demineralization inhibiting agent. Said material is selected from the group consisting of sodium fluoride, stannous fluoride, acidulated phosphate fluoride, calcium fluoride, an amine fluoride, fluoroaluminosilicate glass and any mixture thereof.

Alternatively, the material of the present invention is an amorphous mineral. Said material is selected from the group consisting of amorphous calcium phosphate, amorphous calcium phosphate fluoride, amorphous calcium carbonate phosphate, amorphous calcium carbonate phosphate fluoride, amorphous calcium fluoride and dicalcium phosphate (in a dihydrate form or an anhydrous form).

Alternatively, the material of the present invention is a crystalline mineral. Said material is selected from the group consisting of aragonite, brushite (also known as dicalcium phosphate dehydrate (DCPD)), calcite, dahltite, ferrhydrite, fluoroapatite, hydroxyapatite, lepidocrocite, magnetite, octocalcium phosphate, vaterite, whitlockite, and tri-calcium phosphate, which has an apha and a beta crystalline form.

Alternatively, the material of the present invention is made of an organic material. Said material is selected from the group consisting of macromolecules such as acidic proteins, glycoproteins or sulfated polysaccharides, or smaller molecules such as xylitol, polyaspartic acid or polyglutamic acid.

Alternatively, the material of the present invention is an enhancing agent or further active agent. Said material is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, calcium vaerate, alkali salts, ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate.

Alternatively, the material of the present invention is an acidifying, buffering or pH regulating agent. Said material is selected from the group consisting of acidulated phosphate fluoride, citric acid, sodium citrate, sodium bicarbonate, calcium carbonate, arginine and polyacrylic acid fully neutralized with alkalimetal ammonium or (alkylol) amine compound sodium polyacrylate.

Alternatively, the material of the present invention is an antimicrobial agent. Said material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds.

Alternatively, the material of the present invention serves as a cleaning agent. Said material is selected from the group consisting of sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium laureth carboxylate, sodium dodecyl benzenesulfonate, poloxamers, polyoxyethylene sorbitan esters, fatty alcohol ethoxylates, polyethylene oxide, cocamidopropyl betaine, sodium bicarbonate, monosodiumphosphate, sodium hydroxide, potassium hydroxide, sodium carbonate and imidazole.

Alternatively, the material of the present invention serves as an effervescing agent. Said material uses a sodium bicarbonate/citric acid system.

Alternatively, the material of the present invention serves as a tooth desensitizing agent. Said material is selected from the group consisting of fluorides, potassium citrate, potassium chloride, potassium tartrate, potassium bicarbonate, potassium oxalate and potassium nitrate.

Alternatively, the material of the present invention serves as a tooth whitening or bleaching agent. Said material is selected from the group consisting of hydrogen peroxide, carbamide peroxide metal chlorites, perborates, percarbonates, peroxyacids, persulfates, urea peroxide, calcium peroxide, calcium chlorite, barium chlorite, magnesium chlorite, lithium chlorite, sodium chlorite, potassium chlorite, hypochlorite, chlorine dioxide, sodium percarbonate, oxones, and protease.

According to an aspect of the presently disclosed subject matter, there is provided a substrate having a substrate width dimension, a substrate length dimension and a substrate thickness dimension, the substrate made from a polymeric matrix material and capable of containing: at least one active material having a predetermined intraoral activity, and/or at least one inhibiting material for limiting or stopping demineralization, and/or at least one inactive material; wherein at least one of said substrate width dimension or said substrate length dimension is sufficiently large to enable at least two precursor portions of the substrate to be separated from the substrate, each precursor portion being manipulable to enable altering at least one of the shape and size of the precursor portion to thereby provide a retention device that is configured for being retained at a dental site and for delivering the active material or inactive material to a dental site, said substrate further comprising a plurality of separating facilitators defining separation boundaries between said precursor portions and configured for facilitating separation of respective said precursor portions from a remainder of said substrate.

For example, said separating facilitators comprise at least one first weakened line configured for facilitating separation of each said precursor portion from an adjoining precursor portion For example, said separating facilitators comprise at least one first weakened line configured for facilitating separation of each said precursor portion from an adjoining precursor portion via a respective connector portion therebetween For example, said separating facilitator includes one of the group consisting of the following:
    an indented line;
    a perforated line;
    a physical indicating mark along a separation line; and
    a chemically treated indicating mark along a separation line.

For example, each said precursor portion is at least one of trimmable and foldable to thereby provide the retention device.

For example, the substrate is in the form of a continuous sheet, wherein both said substrate width dimension or said substrate length dimension are sufficiently large to enable at least two precursor portions of the substrate to be separated from the substrate along each one of the width direction and length direction.

For example, the substrate is in the form of a continuous unfolded strip, and said substrate length dimension is sufficiently large to enable a plurality of said precursor portions of the substrate to be separated from the substrate serially along the length direction. For example, said strip has a generally parallelogram shaped plan form. For example, said strip has a generally rectangular shaped plan form. For example, said strip comprises a plurality of serially arranged said precursor portions having a predetermined shape and a precursor width dimension, the precursor width dimension corresponding to said substrate width dimension, wherein adjacent said precursor portions are joined to one another via a connector portion of said substrate having a connector width dimension smaller than said precursor width dimension.

For example, each said precursor portion has a generally circular or oval shape corresponding to a desired final unfolded shape for the retention device.

For example, the substrate comprises at least one of a first set of weakened lines or a second set of weakened lines, wherein the first set of weakened lines corresponds to said separating facilitators and comprises a plurality of first weakened lines configured for facilitating separation of each said precursor portion from an adjoining precursor portion via the respective connector portion therebetween, and wherein the second set of weakened lines comprises a plurality of second weakened lines configured for facilitating folding the respective said precursor portion thereat.

For example, said second weakened lines each comprises bending a facilitator including one of the group consisting of the following:
    an indented, bending line;
    a perforated bending line;
    a physical indicating mark along the bending line; and
    a chemically treated indicating mark along the bending line.

For example, each said precursor portion comprises a body portion and at least one integral handle element transversely projecting from the body portion, wherein each said connector portion is connected to the respective said body portions of adjacent said precursor portions.

For example, the strip is spirally-wound strip and enclosed in a dispensing box.

For example, the substrate is in the form of a continuous folded strip, comprising two parallel at least partially superposed sub-strips in general V-shaped arrangement and joined together at the apex of the V, and wherein said substrate length dimension is sufficiently large to enable a plurality of said precursor portions of the substrate to be separated from the substrate serially along the length direction, and wherein the respective said precursor portions have a folded configuration, comprising pair of flaps in corresponding general V-shaped arrangement and joined together at the apex of the corresponding V.

For example, each said sub-strip has a generally parallelogram shaped plan form.

For example, each said sub-strip has a generally rectangular shaped plan form.

For example, said flaps have the same width dimension.

For example, said flaps have the unequal width dimensions one from the other.

For example, each said flap has a respective free edge spaced from the respective apex, and wherein each said flap comprises respective forward and aft edges, and wherein each said free edge comprises a concave indentation.

For example, said strip comprises a plurality of said concave indentations formed integrally with the respective substrips.

For example, the strip is spirally-wound strip and enclosed in a dispensing box.

For example, the strip further comprising an elongated portion joined to said sub-strips in general Y-shaped arrangement.

For example, each said flap has a respective free edge spaced from the respective apex, and wherein each said flap comprises respective forward and aft edges, and wherein each said free edge is inwardly curled.

For example, said flaps are concurrently curved to provide the retention device in curvate form.

For example, said flaps are concurrently rolled to provide the retention device in rolled configuration.

For example, the precursor portion is further manipulated by folding the flaps over themselves.

For example, the flaps are folded over themselves about an auxiliary fold line generally orthogonal to said apex.

For example, the substrate further comprises stiffening elements embedded in the matrix material.

For example, said stiffening elements comprise a plurality of fibers.

For example, the substrate is in the form of a continuous folded strip, comprising a plurality of sub-strips longitudinally joined to one another in accordion-like cross-section, and wherein said substrate length dimension is sufficiently large to enable a plurality of said precursor portions of the substrate to be separated from the substrate serially along the length direction, and wherein the respective said precursor portions have a folded configuration, comprising a corresponding plurality of flaps in corresponding general accordion-like cross-section.

For example, the polymeric matrix material comprises a hydrophilic polymer such as to enable the respective said retention device to be affixed by swelling in situ by the hydration of the respective matrix in the oral cavity after accommodation of said retention device at the dental site.

For example, said retention device is preferably soft for easy interproximal insertion, and preferably provides a cleaning effect which would serve as an alternative or supplement to flossing and releases at least one antimicrobial or cleansing agent and/or at least one remineralizing and/or at least one mineralizing agent and/or at least one demineralization inhibiting agent.

For example, said retention device is one of: substantially biodegradable, self-degradable, substantially resorbable and substantially non-resorbable.

For example, the matrix material further comprises any one of an enhancing agent for enhancing the application and release of the active material such as plasticizer, elasticizer, coloring agents, adhering agent, filler, softener, binder and preserving or sterilizing agent or any one of an auxiliary agent such as an antimicrobial agent, anti plaque agent, anti inflammatory agent, antioxidant, humectants, nutrient analgesic or anaesthetic agent, anti calculus agent, cleaning agent, effervescent agent, tooth desensitizing agent, staining agent, hemostatic agent, astringent agent, whitening or bleaching agent, flavoring or sweetening agent, breath freshener, or sensate.

For example, the active material is selected from the group consisting of sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, acidulated phosphate fluoride, an amine fluoride, fluoroaminosilicate glass and any mixture thereof, or comprises any other suitable fluoridation agent.

For example, the active material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds, or comprises any other suitable antimicrobial agent.

For example, the active material is any one of a fluoridation agent, an antimicrobial agent, a remineralization agent, a mineralization agent, a demineralization inhibiting agent, a cleaning agent, a tooth desensitizing agent and a tooth whitening/bleaching agent.

According to an aspect of the presently disclosed subject matter, there is provided a mold for manufacturing a substrate having a substrate width dimension, a substrate length dimension and a substrate thickness dimension, the substrate made from a polymeric matrix material and containing at least one active material having a predetermined intraoral activity, wherein at least one of said substrate width dimension or said substrate length dimension is sufficiently large to enable at least two precursor portions of the substrate to be separated from the substrate, each precursor portion being manipulable to enable altering at least one of the shape and size of the precursor portion to thereby provide a retention device that is configured for being retained at a dental site and for delivering said active material to a dental site, the substrate further comprising at least one of a first set of weakened lines or a second set of weakened lines, wherein the first set of weakened lines comprises a plurality of first weakened lines configured for facilitating separation of each said precursor portion from an adjoining precursor portion via the respective connector portion therebetween, and wherein the second set of weakened lines comprises a plurality of second weakened lines configured for facilitating folding the respective said precursor portion thereat, the mold comprising a mold cavity including side walls and a base, complementary to the plan shape of the substrate, the base including raised portions complementary and corresponding to the respective said at least one of the first set of weakened lines or the second set of weakened lines.

According to an aspect of the presently disclosed subject matter, there is provided a method for manufacturing a retention device that is configured for being retained at a dental site and for delivering an active material or an inactive material to a dental site, comprising:

providing a substrate having a substrate width dimension, a substrate length dimension and a substrate thickness dimension, the substrate made from a polymeric matrix material and containing at least one said active material having a predetermined intraoral activity or at least one inactive material, wherein at least one of said substrate width dimension or said substrate length dimension is sufficiently large to enable at least two precursor portions of the substrate to be separated from the substrate, said substrate further comprising a plurality of separating facilitators defining separation boundaries between said precursor portions and configured for facilitating separation of respective said precursor portions from a remainder of said substrate;

separating at least one said precursor portion from the substrate along respective said separating facilitators; and manipulating said precursor portion by altering at least one of the shape and size of the precursor portion to thereby provide the retention device.

BRIEF DESCRIPTION OF THE FIGURES

In the drawings:

FIG. 4(a) illustrates the retention device a configuration comprising notches (or, recesses) to facilitate interproximal placement around the interdental gingival papilla, and extensions (or, protrusions) in order to fill the col area and to overlap the gingival papilla on the exterior portions; FIG. 4(b) illustrates the retention device similar to that shown in FIG. 4(a), in an elongated form to fill an asymmetrical col area; FIG. 4(c) illustrates the retention device shown in FIG. 4(a) with side flaps (or, wing members) which also facilitate retention at an interproximal site and increases the area of contact of the device to a larger area around the contact area; FIG. 4(d) illustrates the retention device in a star shaped configuration, similar in essence to that of FIGS. 4(c) and 4(d); FIG. 4(e) illustrates the retention device in a C-shaped configuration, showing the axes about which the device may be folded to form a symmetrical (Y-Y) shaped device or asymmetrical (Z-Z) shaped device.

FIG. 6(a) illustrates a frontal (facial) device view of a strip with two distal retention devices as shown in FIG. 4(c) in order to retain the said strip between the first bicuspids (premolars) and canines by means of the retention devices which are attached to the strip by means of an extension arm; FIG. 6(b) illustrates a top view of the embodiment of FIG. 6(a) taken along line YY-YY thereof; FIG. 6(c) illustrates a top view of a longer strip that covers the facial side of an entire dental arch with four retention systems.

FIG. 16(a) illustrates in isometric view a matrix formed from a precursor portion in folded configuration; FIGS. 16(b), 16(c), 16(d), illustrate in isometric view the matrix of FIG. 16(a) manipulated into alternative forms.

DETAILED DESCRIPTION

Figure 1A:
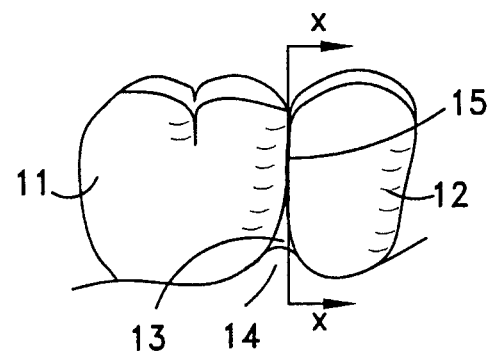
FIG. 1(a) illustrates a side, elevation view of a lingual portion of two lower posterior teeth (a molar and bicuspid (premolar)), showing the space between these two teeth (the interproximal or aproximal space), the gingival papilla and the contact area.

Aspects of the present invention are defined by the claims, the contents of which are to be read as included within the disclosure of the specification, and will now be described by way of example with reference to the accompanying Figures.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

According to certain aspects of the present invention there is provided a device for the controlled or sustained delivery of a material or materials having a predetermined intra-oral activity to dental surfaces of the oral cavity, typically tooth surfaces or carious lesions, and in particular to interproximal sites or furcations, the device comprising a matrix or matrices containing said material or materials. The matrix or matrices is adapted for the controlled or sustained release of the active material or materials, and is further adapted for physically affixing at the dental site, for at least a predetermined time period that is correlated to the delivery of a predetermined portion of said material or materials to said site. This time period typically depends on the nature of the active material or materials and on the subject being treated, and may comprise a few seconds while a chemical activator, an electrical current, or a heat or light source such as a laser is administered to about four to eight hours during interproximal caries prevention or treatment. It is to be appreciated that a major factor in establishing the rate of release of the active material or materials is the structure of the polymeric matrix or matrices as a single uniform unit, multi-layer or a multi-location form. Thus, desired rates of release may be achieved by employing specific polymers, which are preferably cross-linked to a degree affording the desired rate of release. Matrices that are highly cross-linked would release the active material or materials more slowly, and vice versa. The man of skill in the art of pharmacy and delivery system is familiar with such considerations, which are described in many articles and textbooks, e.g., Remington's Pharmaceutical Sciences, Gennaro A. R. ed., Mack Publishing Company, Easton, Pa., 1990, which is fully incorporated herein by reference.

The release of an active agent or agents can be varied within a single matrix or by utilizing a combination of more than one matrix. There are many examples of means for varying release patterns from a single matrix. Examples include different types and degrees of cross-linkage and different additives (such as antimicrobial agents, preservatives, sterilizing agents and enzyme inhibitors) which influence the biodegradation. Furthermore, the release of even a single agent can vary by the manner it is bound in a matrix. For example, sodium fluoride can be released from a single matrix in a biphasic manner where the initial release is of loosely bound sodium fluoride and the next release is of more firmly bound sodium fluoride. Different patterns can also be obtained by using different types of fluoride, for example sodium fluoride, acidulated phosphate fluoride and an amino fluoride, which differ chemically and in molecular size. Another facet is that the matrix can create a microenvironment which excludes some salivary products such as proteins that inhibit mineralization, and others which include mineralization such as calcium phosphate and arginine. The biphasic pattern of sodium fluoride release allows an initial burst of fluoride ions to exchange with hydroxyapatite OH.sup.-groups and accelerate remineralization, then the decrease of fluoride release allows the crystals to grow by providing some fluoride, calcium and phosphate from the matrix. The latter two elements can either be added as agents to the matrix or absorbed by the matrix from the saliva. The final release also favors the deposition of calcium fluoride globules which are long term pH sensitive fluoride reservoirs.

Another approach of varying release patterns is the use of more than one matrix either as separate layers or multilocated systems. Besides causing different release patterns, the use of more than one matrix can keep different agents apart to in situ placement. Each matrix could be loaded with the same or different agent/s that could be released at different rates and/or stages by utilizing intrinsically different matrices at the chemical level or/and physical parameters. For example, the outer layer of a bilayer sphere would first be exposed to the saliva and release, for example, an effervescent cleaning system which loosens and dislodges interproximal plaque and debris and then the inner layer releases, for example, fluoride ions. Another example is the initial release of hypochlorite, which removes organic content of dentinal tubules and then a mineralizing agent or agents. (see Inaba D. et al., Caries Res. 30:218-224 (1996).) Yet another example is that the device can comprise of a coronal and an apical region where the coronal region contains an agent or agents more effective on enamel and the apical region contains an agent or agents more effective on cementum, dentin, gingival and periodontal tissue. An example of a multilayered multi-phase release system is one designed to mimic chiton radula formation which could be used to favorably alter tooth surfaces.

These matrices can comprise a single unit which was affixed one upon the other either by physical pressure or chemical bonding. They can also be formed by plating the first layer and then the same layer is plated over the dried first layer.

The present invention more particularly relates to a retention device for affixing at a dental site within the intraoral cavity, and directed at the chemical treatment of dental surfaces at the site or for chemical and/or physical restoration of the dental surfaces.

Figure 1B:
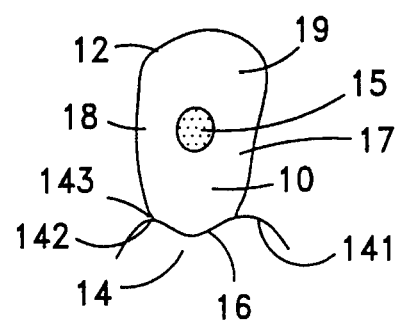
FIG. 1(b) illustrates a cross-sectional view taken along X-X of the embodiment of FIG. 1(a), showing the bicuspid (premolar) with the lingual interdental gingival papillae, the buccal (facial) interdental gingival papillae, the contact area and the gingival col.

Referring to FIG. 1(a) showing a side, elevation view of a lingual portion of a molar 11 and a bicuspid (premolar) 12, and referring to FIG. 1(b) showing a cross-sectional view taken along X-X of FIG. 1(a), an interproximal site 13 is defined herein as comprising both the area of contact 15 which is between two teeth on the medial and distal dental surfaces and the spaces surrounding area of contact 15 on the lingual 17 and buccal (facial) 18 sides of the area of contact 15, as well as at the coronal space 19 and the apical space 10. The apical space 10 is bordered apically by interdental gingival papillae 141 and 142 on the lingual 141 and buccal (facial) 142 surfaces and by a valley known as the col 16, which is the central apical base of the interproximal site 13, and which spans the interdental gingival papillae 14. The apical space 10 also includes the gingival sulcus 143 which surrounds the tooth 12 (see Glickman I Clinical Periodontology 4.sup.th Ed Saunders pg 18-19). The morphology and size of the above mentioned spaces are determined by the tooth size, position and shape. For instance, the contact area in the posterior teeth is located nearer the buccal surface 18 which causes a larger lingual gingival papilla 141. The contact area in anterior teeth is located nearer the lingual surface, which causes a larger lingual papilla (see Gilmore H W et al, Operative Dentistry, 3.sup.rd Ed., CV Mosby Company, pg. 25-26). Furthermore, the permanent anterior interdental papillary widths are less than those of the permanent molars which range from about 14 mm to 5 mm. Obviously, primary (milk) teeth also have smaller interdental papillary width dimensions. Additionally, diseases can also cause variations in shape and size. For example, periodontal disease increases the size of the spaces because of gingival and bone loss, however, on the other hand, spaces can be reduced due to gingival swelling.

It should be noted that the contact area is erroneously referred to in conventional literature as a contact point, like two marbles making contact. This is often not the case, since attrition causes the contact to flatten, and the teeth to move, which results in a contact area of about 0.3-1.0 mm$^2$ in the posterior teeth, and smaller areas in anterior and milk teeth. (see Gilmore H W, et al, op cit.)

The term, "dental surface" is defined herein as referring to any portion of a tooth or portion of the gingiva, particularly at interproximal sites and furcations.

The term, "reshape" as used herein refers to the act of reducing the overall dimensions of an object, for instance by bending, folding, rolling or otherwise collapsing the object to a desired configuration (shape), physically or chemically. To that end, the terms, "collapsing", "bending", "folding", "rolling", "cutting", etc. particularly refer to or facilitate the reshaping of the device of the present invention to allow the device to fit in an area of a dental site that is smaller in at least one dimension than that of the device in its original shape (e.g. prior to reshaping).

The term, "dental site" as used herein refers in general to interproximal sites and furcations. More specifically, the dental sites referred to herein comprise at least a space between adjacent dental surfaces, such that with reference to the interproximal site, the dental site includes at least a portion of the spaces (e.g. the apical space) surrounding the area of contact, and in some cases, includes the area of contact as well.

According to the present invention, in at least the reshaped configuration, the retention device is preferably shaped in an anatomical configuration HH according to the contours of the dental surfaces at the sites at which the device is affixed.

Figure 2A:
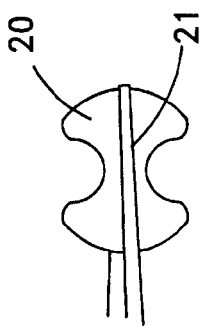
FIG. 2(a) illustrates a first embodiment of the retention device of the present invention in an H-shape.
Figure 2B:
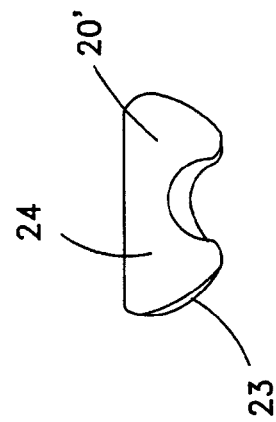
FIG. 2(b) illustrates the retention device of FIG. 2(a) gripped along the centerline of the device by the tip of tweezers.
Figure 2C:
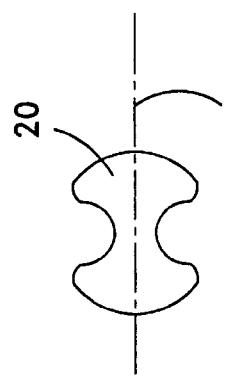
FIG. 2(c) illustrates the direction in which the retention device of FIG. 2(a) is folded while being gripped along the centerline by tweezers.
Figure 2D:
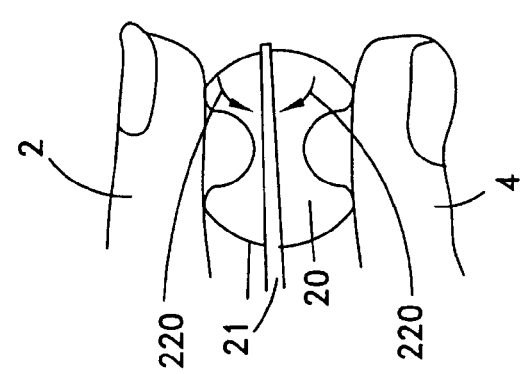
FIG. 2(d) illustrates the retention device in a folded configuration.

Thus, in a first aspect of the first embodiment of the present invention, and referring to FIGS. 2(a) to 2(f), the retention device 20 comprises a polymeric matrix containing an active material, and, in the first aspect, has an H-shape. Retention device 20 is folded as described herein below, for affixing at a dental site, typically below area of contact 15, and in some cases also at area of contact 15, depending on the morphology of the interproximal area, the rigidity of the device and operative procedures. Referring to FIG. 2(b), retention device 20 may be gripped along its longitudinal centerline (or, bending line) 22 (see FIG. 2(a)) by the tip of thin tweezers 21. Since retention device 20 may be stiff (and cracked if bent when dry) tweezers 21 are preferably first dampened, for instance with a water syringe from a dental unit or by dipping into a container of water prior to gripping, to allow retention device 20 to soften along the axis about which the folding is performed. As seen in FIG. 2(c), while gripping retention device 20 with tweezers, 21, the user additionally holds the outer edges of retention device 20 with fingers 2, 4, and applies enough force to fold the outer edges toward each other as indicated by arrows 220, thereby forming two flaps 23, 24, as shown in FIG. 2(d). Preferably, each outer edge is folded inwards to form an angle of approximately 30°. between flaps 23, 24, however, retention device 20 may be folded more or less than 30°, and may be rolled or folded over more than once, depending, among other things, on the size of the interproximal site. Referring to FIGS. 2(e) and 2(f), folded retention device 20' is inserted interproximally in an "A" (or, upside down "V") orientation. When fixated interproximally, the apex of the "A" is situated below or at contact area 15 of adjacent teeth 11, 12, and the outer surface of flaps 23, 24 rest along the mesial and distal tooth surfaces. The inner surface of flaps 23, 24 arch over gingival 14. When absorbing the moisture and fluids in the intraoral cavity, the device softens and expands in situ, thereby causing device 20' to essentially fill all or some of the space of the interproximal site 13.

Figure 3A:
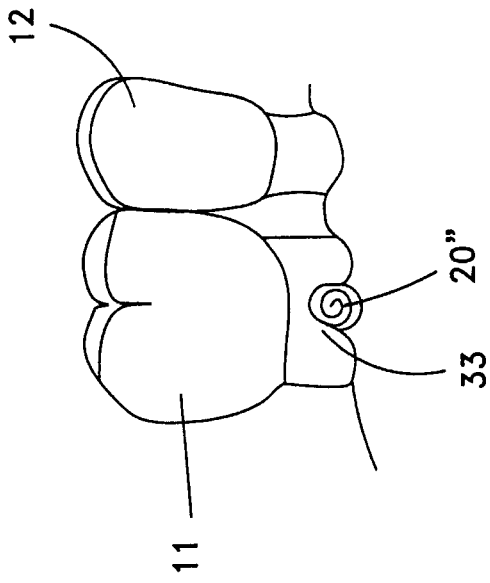
FIG. 3(a) illustrates a side elevation view of a bucal portion of two lower posterior teeth similar to that shown in FIG. 1(a) and FIG. 2(e), showing periodontal disease resulting in gingival and bone recession, and showing a rolled retention device being inserted with tweezers into a furcation of a molar tooth.
Figure 3B:
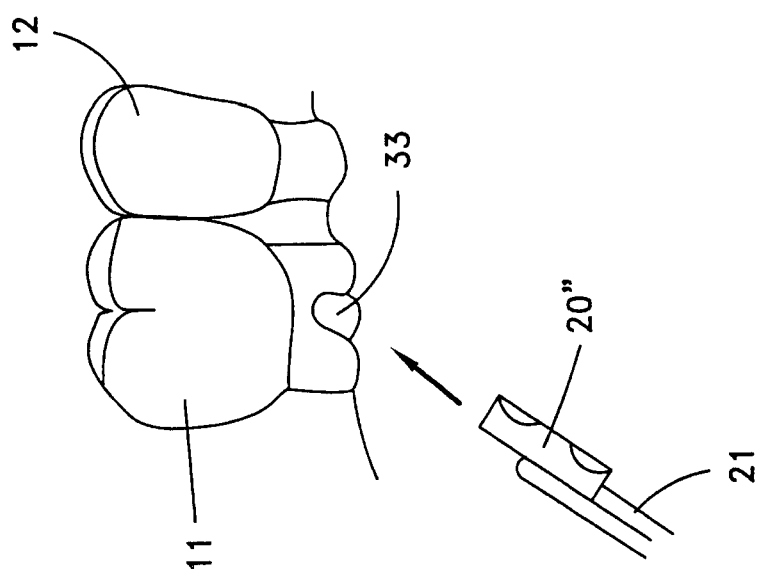
FIG. 3(b) illustrates the rolled retention device in situ, positioned in the furcation.

FIGS. 3(a) and 3(b) show the first aspect of the first embodiment, wherein the retention device 20" is in a rolled configuration for physically affixing in a furcation 33 using a tweezer. FIG. 3b shows rolled device HH physically fixed in the furcation 33 of the molar. When absorbing the moisture and fluids in the intraoral cavity, the device softens and expands in situ, thereby causing device 20" to essentially fill all or some of the space of the furcation 33.

A second aspect of the first embodiment is shown in FIG. 4(a), in which retention device 42 is shaped according to the contours of the apical space of the interproximal site. Retention device 42 comprises slightly convex transverse edges 43 (although straight or concave edges may be desirable in some cases), and longitudinal edges 44 comprising notches (or, recesses) 420 to accommodate the interdental gingival papilla, and extensions (or, protrusions) 422 to enhance retention at the dental surfaces, and a central extension 421 to fill the col area and also enhance retention. Alternatively, extension 422 may be excluded, elongated or shortened, and the cross-sectional shape need not be straight but can be concave on one or both surfaces. Alternative shapes for conforming to the anatomy of different dental surfaces (e.g. interproximal sites) may be desired. For example, anterior and posterior spaces differ in size and in shape from each other. Specifically, the posterior areas are wider, the position of the col is not at the midpoint, and the buccal and lingual gingival papilla are not the same size.

FIG. 4(b) illustrates an alternative aspect of the second aspect, wherein notch 424 is elongated to conform to the anatomy of posterior teeth interdental gingival papillae.

Furthermore, the second aspect can comprise the apical and coronal portion differing in shape. For example, the coronal portion can be straight or dome shaped and the apical portion can be anatomically shaped, like that of FIGS. 4(a)-4(d).

FIG. 4(c) shows the second aspect of the first embodiment, wherein the retention device has wing members 430 for contacting the buccal and lingual tooth surfaces. Alternative structures may be used instead of wing members to facilitate retention at the interproximal site, and increase the contact of the retention device to a larger area around the contact area.

FIG. 4(d) shows a third aspect, wherein retention device 40 is shaped in a star-shape, which is essentially similar to the embodiment shown in FIG. 4(a), but with concave edges, instead of convex edges, and which may be reshaped for affixing at a dental site; FIG. 4(b) shows a fourth aspect, showing a C-shaped retention device 41 which can be folded, for example, along Y-Y to form a symmetrically folded device, or along Z-Z to form an asymmetrically folded device. Other variations (not shown) include a star-shaped device that is elongated (i.e. stretched) in at least one plane.

Preferably according to all aspects of the first embodiment, retention device is designed to facilitate bending or folding. For example, the bending line may be indented along the entire length, or indented or punctured at intermittent points or lines (i.e. perforations) across at least a portion of the length of the bending line. Alternatively, a marking such as a line may be situated along the surface of the retention device to indicate the preferred axis about which retention device should be folded, for instance, in order to form the desired flaps. This line can be a physical form of an area which has been chemically treated to facilitate folded.

The present invention includes other aspects not shown in the figures or described herein, such as a palette shape (see U.S. Design applications No. 29/234,883 by the present inventors). Furthermore, the surfaces of the device may be flat, or one or more surfaces may be concave or convex, or any combination thereof of shapes.

Figure 5B:
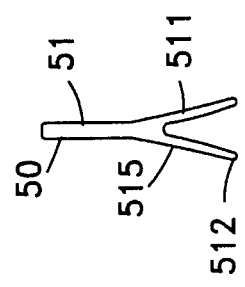
FIG. 5(b) illustrates a cross-sectional view of the embodiment of FIG. 5(a) taken along line XX-XX.
Figure 5A:
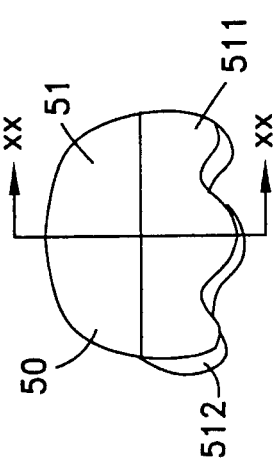
FIG. 5(a) illustrates a front view of the retention device in a Y-shape in an upside down orientation, which is anatomically contoured at the two apical portions, and slightly concaved at the portion for positioning at the contact area.

A second embodiment of the present invention, comprising all of the advantages and features of the first embodiment, mutatis mutandis, is shown in FIGS. 5(a)-5(d), with the following differences. As seen in the figures, particularly FIG. 5(b) showing a cross-sectional view taken along XX-XX of FIG. 5(a), retention device 50 is Y-shaped, for inserting and affixing in an upside down orientation at an interproximal site (FIG. 5(c)) such that the elongated portion 51 is disposed at contact area 513, and the "A" portion 515 is disposed beneath contact area 513 of adjacent teeth 52, 53, wherein flaps 511, 512 contact adjacent dental surfaces. Flaps 511 and 512 are designed to be bent slightly towards one another in order to be placed interproximally, whereafter flaps 511, 512 press slightly away from one another towards adjacent dental surfaces, thereby enhancing fixation of retention device 50 at the interproximal site. Included in this embodiment are modifications of the above description, for example, a device that only incorporates the "A" portion 515, without elongated portion 51.

Figure 5D:
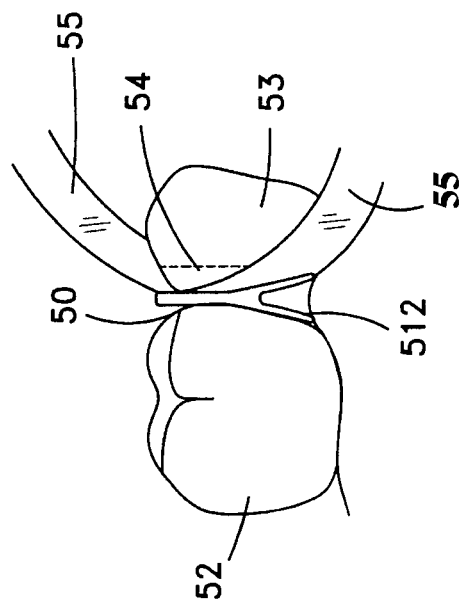
FIG. 5(d) is a side elevation view similar to FIG. 1(a) showing a matrix band being held in situ by a Y-shaped retention device between the molar and bicuspid (premolar) in order to facilitate restoration of the cavity.
Figure 5C:
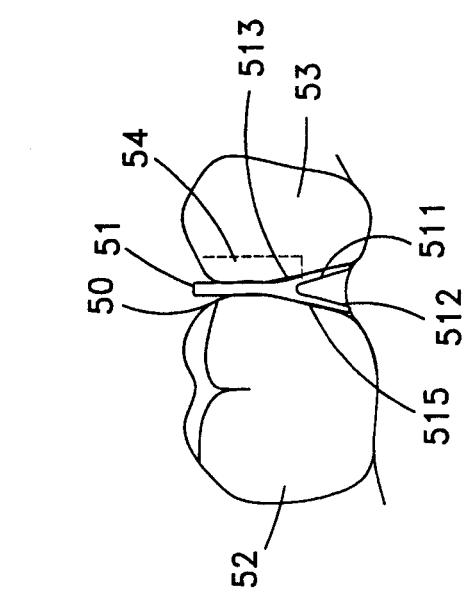
FIG. 5(c) is a side elevation view similar to FIG. 1(a) showing the device of FIG. 5(a) in situ between the molar and bicuspid (premolar), which has a distal cavity in the bicuspid that requires a restoration.

According to one aspect of the second embodiment of the present invention and referring to FIGS. 5(c) and 5(d) retention device 50 can be made of a metal or plastic material for fixation at an interproximal site, in order to facilitate the restoration of a cavity 54 with an appropriate restoration material such as a tooth colored resin, glass ionomer or amalgam, independently, as shown in FIG. 5(c) or with a matrix band 55 as shown in FIG. 5(d). When flaps 511 and 512 push towards adjacent dental surfaces as described above, retention of matrix band 55 is facilitated.

A third embodiment of the present invention, comprising all of the advantages and features of the first and second embodiments, mutatis mutandis, is shown in FIGS. 6(a)-6(c), with the following differences. The third embodiment comprises a system of folded retention devices 62 attached directly or via at least one short or long extension arm 64 to an elongated strip 61 having the form of at least a portion of an entire dental arch, to allow a plurality of devices to be essentially simultaneously inserted to a dental site. FIG. 6(b) shows a cross-sectional view taken across line YY-YY of FIG. 6(a), showing strip 61 covering the facial portion of anterior teeth 63. FIG. 6(c) shows a top view of a strip 65 corresponding to an entire dental arch 65.

According to another aspect of the invention there is provided a method and system for providing the device, or at least the matrix of the retention device, in which the matrix initially forms part of a larger continuous substrate, the substrate being provided in the form of a continuous sheet, having a width dimension W and a length dimension L, and also a thickness dimension T. The substrate is made from the desired matrix material, and can optionally include one or more active agents and/or one or more inactive agents already in the matrix. According to this aspect of the invention, a portion (referred to herein as a "precursor portion") of this substrate can be removed from the remainder of the substrate, and this precursor portion becomes the matrix that can then be used in the oral cavity. For example, the precursor portion can be manipulated to alter its shape and size, for example by folding and/or cutting the precursor portion, to enable the resultant matrix to fit, fill or otherwise conform to the interproximal site in which it is implanted, whether the interproximal site is normal and abnormal, thereby harmonizing the form of the matrix with the anatomical nuances and/or structural changes caused by pathology. In at least some cases, the precursor portion constitutes the matrix, which can then be further manipulated to insert the same into the dental site. The substrate and/or the precursor portion can be initially unfolded, and the resulting matrix is folded to provide a folded configuration, or, the substrate and/or the precursor portion can be partially or fully folded, and the resulting matrix is that correspondingly folded in the folded configuration. In any case, in the folded configuration, at least two flaps are superposed one on the other, partially or fully, and joined together at an edge.

For example such a matrix can have a form and function, made from the same materials and comprising similar agents to, and used in a similar manner to the embodiments of the matrices disclosed above, in particular with reference to FIGS. 1(a) to 6(c), mutatis mutandis. For example, the respective matrix can have any suitable shape (e.g. planform) including for example circular, oval, square, rectangular, hexagonal, pentagonal, octagonal, or other polygonal. For example, the size of the respective matrix can vary—for example the matrix can be 20% to 40% smaller in linear dimensions for deciduous teeth than for regular teeth. For example, the respective matrix can be of uniform thickness, or can have a varying thickness, for example wedge shaped in transverse cross-section, which can facilitate interproximal insertion. Optionally, the respective matrix can be provided with one or more bending facilitators, in symmetrical or non-symmetrical arrangement with respect to the matrix.

Figure 7A:
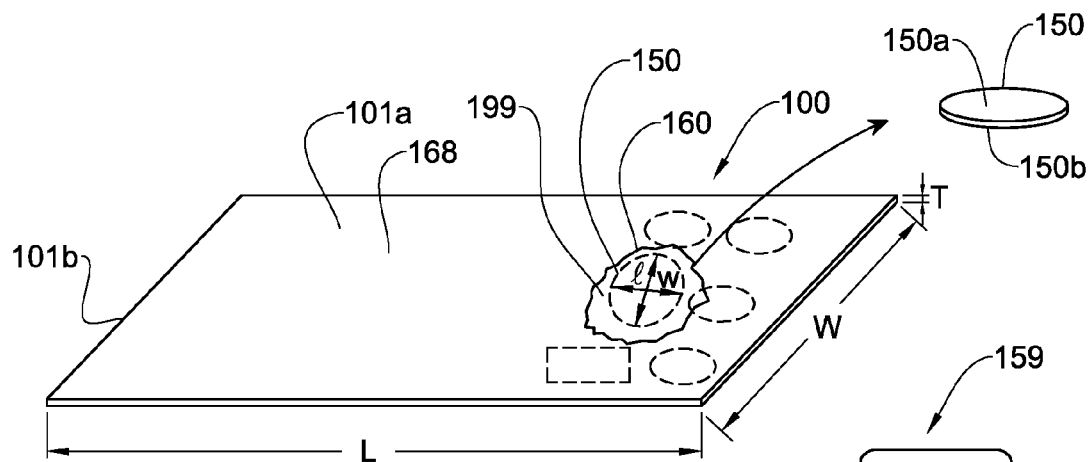
FIG. 7(a) illustrates in isometric view a first example of a substrate according to an aspect of the invention.

In a first example, and referring to FIG. 7(a), a substrate 100 is provided in the form of a continuous unfolded sheet, having a width dimension W, a length dimension L, and a thickness dimension T. The width dimension W and the length dimension L are each greater than the corresponding width dimension w and a length dimension l of the unfolded matrix 150 that it is wished to obtain from the substrate 100. The substrate 100 has opposite facing sides 101a, 101b, corresponding to the opposite facing sides 150a, 150b of the unfolded matrix 150. A user, such as for example a dental practitioner or the patient, can separate the matrix 150 from the remainder 168 of the substrate 100 by, for example, first cutting, folding at least once and then snapping apart, or tearing or otherwise separating a precursor portion 160 of the substrate 100. The substrate further comprising a plurality of separating facilitators 199 defining separation boundaries between the precursor portions and the remainder of the substrate or between adjacent precursor portions. The separating facilitators 199 are configured for facilitating separation of respective said precursor portions from a remainder of said substrate. The separating facilitators 199 can be in the form of visual marks marking the periphery of the shape of the precursor portion 160, and/or can include a weakened line along this periphery, for example.

This precursor portion 160 can be larger than the desired matrix 150, and the user can further trim and/or re-shape the plan form of the precursor portion 160 to arrive at the desired shape for the matrix 150. Alternatively, the precursor portion 160 can be initially separated from the remainder of the substrate 100 with the desired shape, and thus initially constitutes the unfolded matrix 150. In this example, the width W and/or the length L is such as to allow a plurality of precursor portions 160 or matrices 150 to be removed from the substrate 100, for example along the width direction and/or along the length direction. The plurality of matrices 150 can all have the same shape and size, or each matrix 150 can have a different shape and/or size. For example, the shape and/or size of at least one such matrix 150 can correspond to the shape and/or size, respectively, of the examples of matrices disclosed above and illustrated in FIGS. 2(a) to 6(c), mutatis mutandis.

In any case, the matrix 150 is initially in an unfolded or generally flat state at least initially after being formed from the precursor portion 160 which is formed from the substrate 100, or when directly separated from the substrate 100.

Figure 7B:
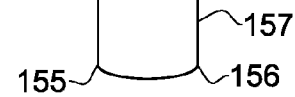
FIG. 7(b) illustrates in isometric view an example of a tool useful for separating a precursor portion from the substrate of FIG. 7(a).

Optionally, and referring to FIG. 7(b), a tool 159 can be provided for facilitating removing the matrix 150 directly, or alternatively for removing the precursor portion 160, from the substrate 100. The tool 159 has a handle 158 that is configured to be grasped by the hand of a user to manipulate the tool, and a cutting end 157 having a peripheral wall including peripheral cutting edge 156 shaped correspondingly to the desired shape and size of the matrix 150, or alternatively of the precursor portion 160, which can then be further worked on to provide the matrix 150. The cutting edge 156 defines an opening to a recess 155, extending inwardly into the cutting end 157, away from the cutting edge 156. The cutting edge 156 can be, for example, a sharp edge and thus the tool 159 can be used as a punch to directly cut the matrix 150 from the substrate 100 by pressing the tool 159 generally perpendicularly onto the substrate. Alternatively, for example, the cutting edge 156 can have a serrated edge, and thus a rotational movement of the tool 159 (for example about an longitudinal axis of the tool) when in contact with the substrate 100 can be used for removing the precursor portion 160, which is circular in shape; the precursor portion 160 can then constitute the matrix 150, or can be cut further and reshaped as desired to provide the unfolded matrix 150. Alternatively, for example, the cutting edge 156 can comprise a plurality of sharp pins arranged along the periphery; pressing the tool 159 onto the substrate via cutting edge 156 causes the pins to form closely-spaced perforations on the substrate 100, and the perforations are arranged in the desired shape of the matrix 150 or of the precursor portion 160. The matrix 150 can then be removed directly manually, for example, from the substrate by tearing the material between adjacent perforations. In this example, the strip 100 is of uniform thickness throughout, Such a tool can thus provide the separating facilitators 199 to the substrate, for example.

Referring to FIG. 7(b), tool 159 can optionally include an internal serrated edge, for example internally spanning the recess 155, and the internal edge can provide indentations, serrations, or an otherwise weakened fold line, to facilitate folding about such a fold line, for example as shown in the example of FIGS. 2(a) and 2(d).

Figure 8A:
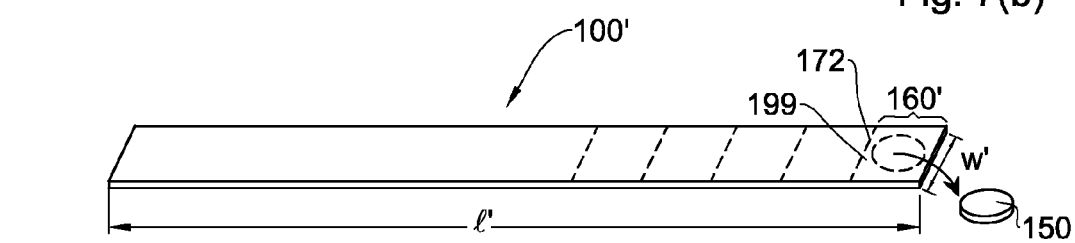
FIG. 8(a) illustrates in isometric view a second example of a substrate according to an aspect of the invention.

In a second example, and referring to FIG. 8(a), the substrate 100 is provided in the form of a continuous unfolded strip 100', having a width w' and length l'. In this example, the strip is generally rectangular, and precursor portions 160' of the strip having a width w' and any desired length up to length dimension l' can be separated from the strip 100', for example by cutting or tearing off or otherwise removing the precursor portion 160' along the corresponding separating facilitators 199. For example, such precursor portions can have any desired shape, for example a serially repeatable shape, for example a parallelogram, or square, or rectangular, having an aspect ratio over 1.0, for example up to 2.0 or up to 3.0, or having an aspect ratio less than 1.0, for example 0.5 or 0.8. To facilitate identifying and/or separating each precursor portion 160' serially from the trip 100', the strip 100' can optionally be marked at intervals with separating facilitators 199 in the form of lines 172, in which the spacing between adjacent pairs of lines 172 corresponds to the desired width for the respective precursor portion 160'. The lines 172 can be etched, engraved, or otherwise formed including a physical weakness along which it is easier to fold and/or cut the strip 100', or the lines 172 can each be formed as an optical mark, for example having a color and/or contrast different from the remainder of the strip 100'. After the precursor portion 160' is separated from the strip 100', it can be cut further and reshaped as desired to provide the matrix 150. In this example, the strip 100' is of uniform thickness throughout.

Figure 8B:
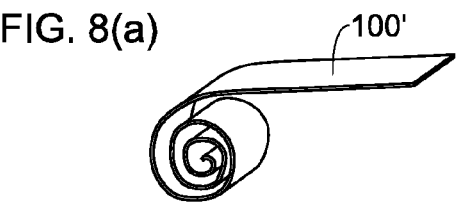
FIG. 8(b) illustrates in isometric view the example of FIG. 8(a) in spiral wound configuration.
Figure 8C:
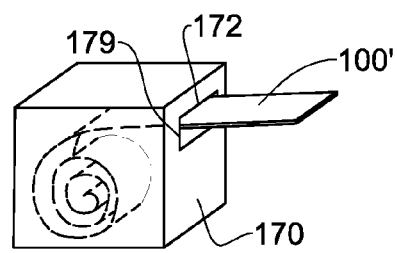
FIG. 8(c) illustrates in isometric view the example of FIG. 8(b) wherein the spiral wound configuration is accommodated in a dispensing box.

Optionally, the strip 100' can be rolled along the length direction (i.e., about an axis parallel to the width direction) into a compact spiral form, for example as illustrated in FIG. 8(b). The spirally-wound strip 100' can be optionally enclosed in a dispensing box 170, for example as illustrated in FIG. 8(c), the box 170 having an opening 172 from which a leading edge of the strip 100' can project. The box 170 can be used as a dispenser, in which precursor portions 160' of the strip can be serially removed by extracting the leading edge of the strip 100' through the opening 172 and then cutting off the desired length of strip 100'. Optionally, a cutting edge 179 can be provided in the box 170, at the opening 172, to facilitate cutting the precursor portions 160' from the strip 100'. In any case, the matrix 150 provided from the precursor portion 160' can have smaller width and length dimensions than the respective precursor portion 160', for example. Again, as in the first example, mutatis mutandis, the matrix 150 is initially in an unfolded or generally flat state at least initially after being separated from the precursor portion 160' or the strip 100'.

Any suitable method can be used for the manufacture of the strip 100 of the example of FIG. 7(*a*) or for the manufacture of the strip 100' of the example of FIG. 8. For example, the matrix material in liquid form can be poured into a suitable mold, such as for example a flat tray defining a mold cavity complementary in shape to the shape of the desired strip 100 or strip 100'. Once the matrix material dries the desired strip 100 or strip 100' can be peeled off fully from the mold ready for use, or can be dispended from the mold as needed. Alternatively, the mold cavity is larger than the desired strip 100 or strip 100', and thus the strip 100 or strip 100' is cut off from the dried matrix via the separating facilitators 199 to the desired dimensions.

In any case, optionally, a removable film can be provided in the respective mold cavity, so that the matrix material is poured onto the film in the mold cavity. For example, such a film can include a wax paper sheet or a thin plastic film. When the matrix material is dry, it can be removed together with the film, which is temporarily adhered thereto, and can be peeled off when desired or left attached thereto and inserted into the intra oral site to be left therewithin or removed thereafter to leave the matrix in place.

Figure 9:
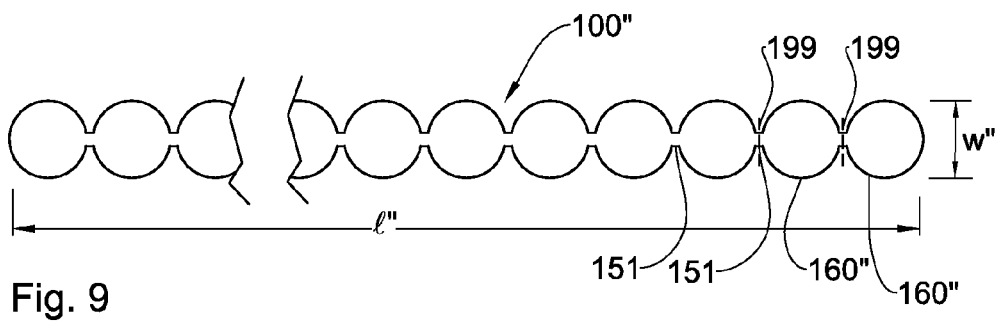
FIG. 9 illustrates in top view a third example of a substrate according to an aspect of the invention.

In a third example, and referring to FIG. 9, the substrate 100 is provided in the form of a continuous unfolded strip 100", having a maximum width dimension w" and a length dimension l", similar to the second example, mutatis mutandis, but with some differences. In this example, the strip 100" comprises a plurality of serially arranged connected precursor portions 160". Each precursor portion 160" of the strip has a generally circular or oval shape corresponding to a desired final shape for the matrix 150, has a width w" and length, and is connected to an adjacent precursor portion 160" via an interface, for example in the form of a bridge or tab 151 having a width dimension significantly smaller than width dimension w". Each precursor portion 160" can be separated from the strip 100", for example by cutting or tearing off the precursor portion 160" from the next precursor portion 160" on the strip 100" at the shared tab 151, which thus operates as the respective separating facilitators 199. Since the precursor portions 160" already have the desired shape of the matrix 150, once separated from the strip 100", the precursor portions 160" constitute the respective unfolded matrices 150. Alternatively, after a precursor portion 160" is separated from the strip 100", the precursor portion 160" can be cut or trimmed further, and optionally folded, and reshaped as desired to provide the desired shape and size for the resulting matrix 150. In this example, the strip 100" is of uniform thickness throughout.

Optionally, the strip 100" can be rolled a into a compact spiral form, and further optionally, the spirally-wound strip 100" can be optionally enclosed in a dispensing box, for example as disclosed for the second example, mutatis mutandis.

The example of the strip 100" illustrated in FIG. 9 can be manufactured using similar methods to those directed at the first and second examples, mutatis mutandis.

In an alternative variation of the third example, and referring to FIGS. 10(*a*) and 10(*b*), the strip 100" is formed having a first set and/or a second set of weakened lines.

The first set of weakened lines corresponds to the respective separating facilitators 199, and comprises a plurality of first weakened lines 174, which facilitate separation of the respective precursor portion 160" from the remainder of the strip 100". Each first weakened line 174 is provided at a respective tab 151, along the width direction, and can comprise any suitable configuration to provide a weaker mechanical integrity than that of the precursor portions 160". For example, each first weakened line 174 can comprise one or more of the following: a reduced thickness as compared to the thickness of the precursor portion 160"; a plurality of perforations; a chemical agent that reduces the mechanical integrity of the matrix material; laser treatment to weaken or mark the line. For example, such chemical agents can include one or more of: water, alcohol, enzymes, digestive chemicals, saliva, or other chemicals or mixtures thereof.

The second set of weakened lines comprises a plurality of second weakened lines 176, which facilitate folding the respective matrix 150 thereat. In the illustrated example, a single second weakened line 176 is provided at each respective precursor portion 160", along the width direction and at the center of the precursor portion 160", i.e. in an orthogonal transverse direction to the longitudinal (length) direction of the strip 100". However, other configurations for the second weakened line 176 are also possible. For example, a number of second weakened lines 176 can be provided for each precursor portion 160", allowing for the final matrix 150 to be folded about multiple fold lines. Additionally or alternatively, at least one second weakened line 176 can be provided along a direction different from the width direction— for example along the length direction (for example running along the entire length of the strip 100") or obliquely thereto. Additionally or alternatively, at least one second weakened line 176 can be provided such as to divide the precursor portion 160" in equal parts, for example as illustrated in FIGS. 10(*c*) to 10(*e*), or in unequal parts so that when folded the resulting matrix 150 is asymmetrical, for example as illustrated in FIGS. 10(*f*) to 10(*h*). In any case, each second weakened line 176 can comprise any suitable configuration to provide a weaker mechanical integrity than that of the precursor portions 160". For example, each second weakened line 176 can comprise one or more of the following: a reduced thickness as compared to the thickness of the precursor portion 160"; a plurality of perforations; a chemical agent that reduces the mechanical integrity of the matrix material; laser treatment to weaken or mark the line. For example, such chemicals agents can include one or more of: water, alcohol, enzymes, digestive chemicals, saliva, or other chemicals or mixtures thereof.

Alternatively, each second weakened line 176 can have the same mechanical integrity as the remainder of the precursor portion 160", and comprises instead a visual mark or other facilitator to guide the user and facilitate folding.

Typically, the mechanical integrity of the second weakened lines 176 is greater than that of the first weakened lines 174.

The example of the strip 100" illustrated in FIGS. 10(*a*) and 10(*b*) can be manufactured using similar methods to those directed at the first and second examples, mutatis mutandis, to initially provide the strip 100" with uniform thickness, and the strip 100" can be subsequently processed to provide the plurality of first weakened lines 174 and/or the plurality of second weakened lines 176. For example, this post-processing step can comprise chemically and/or physically treating the strip to provide the weakened lines. Alternatively, the strip 100" can be cut from or stamped from a larger sheet of matrix material using cutters or a stamp, and the weakened lines provided either concurrently with or subsequent to the separation of the strip 100" from the aforesaid larger sheet.

Alternatively, the of the strip 100" illustrated in FIGS. 10(*a*) and 10(*b*) can be manufactured using similar methods to those directed at the first and second examples, but with some differences, mutatis mutandis, configured to ensure that the plurality of first weakened lines 174 and/or the plurality of second weakened lines 176 (depending on whether it is wished to provide the strip 100" with one or another or both sets of weakened lines) are integrally formed with the strip 100". Referring to FIG. 10(*i*), for example, a mold 190 is provided for casting the strip 100" therein. The mold 190 comprises a mold cavity 191, essentially complementary to the shape of the strip 100". Thus, and referring also to FIGS. 10(*a*) and 10(*b*), the mold cavity 191 comprises a planar base surface 192 corresponding to the lower face 177*b* of the strip 100", and peripheral walls 193, the lower portion 193*a* of which corresponding to the edges 171 of the strip 100". Projections 194 and/or 196 are provided (depending on whether it is wished to provide the strip 100" with one or another or both sets of weakened lines) which project upwards base surface 192, and are complementary in form to, and in the corresponding positions of, the plurality of first weakened lines 174 and the plurality of second weakened lines 176. The peripheral walls 193 optionally have a marking 198 defining a plane corresponding to the upper face 177*a* of the strip 100". In use, suitable matrix material in liquid or other fluid form, for example as disclosed herein (for example see below "The Matrix and Cross-Linking Agents") is poured into the mold cavity, up to the marking 198. Thereafter, the material is allowed to set, and can then be removed from the mold.

For example, the molds 190 can be reusable, or can be configured as disposable, i.e., made from suitable mold materials that are nevertheless cheap economically, as compared with the costs of the matrix material. Optionally, the strip 100" can be provided to users while in the mold 100", allowing the strip 100" or part thereof to be removed by the user when required.

Alternatively, the strip 100" can be formed having non-uniform thickness. For example, referring to FIGS. 10(*j*) and 10(*k*), each precursor 160" can have a wedge-shaped longitudinal cross-section, and can for example be made by using a mold 190' comprising a mold cavity 191', essentially complementary to the shape of the strip 100". In alternative variations of this example, and referring to FIG. 10(*l*), the strip 100" can be formed having a plurality of precursor portions 160" in an array, for example set out in rows and columns of precursor portions 160" joined to adjacent precursor portions via a corresponding plurality of separating facilitators 199 in the form of tabs 151. The precursor portions 160" can be in rectangular array arrangement as illustrated in FIG. 10(*l*), or in hexagonal or other two-dimensional arrangement. A first set of weakened lines is provided comprising a plurality of first weakened lines 174, which facilitate separation of the respective precursor portion 160" from the remainder of the array-shaped strip 100", and an optional second set of weakened lines, comprising a plurality of second weakened lines 176, facilitate folding the respective matrix 150 thereat.

Figure 2:
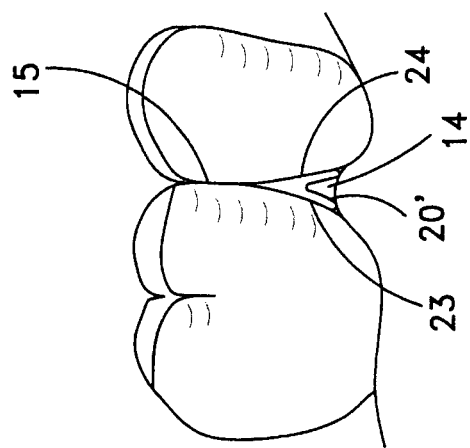
FIG. 2(e) illustrates a side elevation view of a buccal portion of two lower posterior teeth similar to that shown in FIG. 1(a), showing the folded retention device being inserted interproximally while being gripped by tweezers.
FIG. 2(f) illustrates the folded retention device positioned interproximally.
Figure 2:
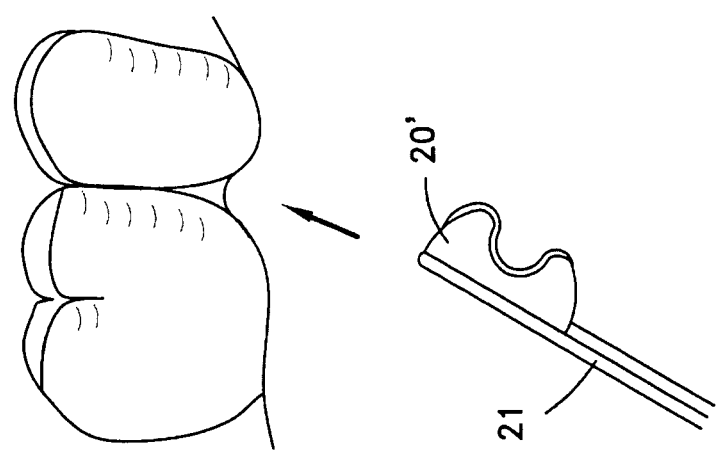

In any case, in each of the first, second and third examples above, or alternative variations thereof, once the respective matrix 150 is directly removed from, or formed from the respective precursor portion that in turn is removed from the respective substrate 100, facilitated by the respective separating facilitators 199, the unfolded matrix can be folded or bent about a fold line to provide a folded configuration than can then be inserted into the dental site, for example an interproximal site 13 (see FIG. 1(*a*)), for example as illustrated in FIG. 2(*f*), mutatis mutandis. The fold line can be real, including a visual mark or comprises a facilitator such as an etched, perforated or otherwise weakened line, for example as described for the example illustrated in FIG. 10(*c*), mutatis mutandis. Alternatively, the fold line can be imaginary, and the user folds the matrix where desired.

In a fourth example, and referring to FIGS. 11(*a*), 11(*b*) and 11(*c*), the substrate 100 is also provided in the form of a continuous unfolded strip 100''', having a maximum width dimension w''' and a length dimension l''', and is similar to the second or third examples, mutatis mutandis, but with some differences. In this example, the strip 100''' comprises a plurality of serially arranged connected precursor portions 160'''. Each precursor portion 160''' of the strip has a body portion 161''' that is similar to precursor portion 160''' of the third example, mutatis mutandis, and has a generally circular or oval shape corresponding to a desired final shape for the matrix 150, has a width w''' and length, and is connected to an adjacent precursor portion 160''' via the respective separating facilitator 199 in the form of an interface, for example in the form of a bridge or tab 151''' having a width dimension significantly smaller than width dimension w'''. Each precursor portion 160''' can be separated from the strip 100", for example by cutting or tearing off the precursor portion 160''' from the next precursor portion 160''' on the strip 100''' at the shared tab 151'''.

In addition, precursor portion 160''' further comprises an integral handle element 163''' transversely projecting from the body portion 161''' and co-planar therewith while still on the strip 100'''. Handle element 163''' can have any suitable shape, for example circular or oval, and is generally the same size or is smaller than the body portion 161'''—for example, the ratio of the plan area of the handle element 163''' to the plan area of the body portion 161''' can be in the range 0.05 to 1.0, for example 0.05, 0.1, 0.2, 0.3, 0.4, 0.5, 0.6, 0.7, 0.8, 0.9 or 1.0. In particular, and as will become clearer below, the handle element 163''' is shaped and sized to facilitate grasping the precursor portion 160''' by the handle element 163''', particular when the handle element 163''' is folded.

As with the third example, mutatis mutandis, since the precursor portions 160''' already have the desired shape of the matrix 150, once separated from the strip 100''' via the separating facilitators 199, the precursor portions 160''' can constitute the respective matrices 150. Alternatively, after a precursor portion 160''' is separated from the strip 100''', the precursor portion 160''' can be cut or trimmed further, and reshaped as desired to provide the desired shape and size for the resulting matrix 150. In this example, the strip 100''' is of uniform thickness throughout.

The handle element 163''' can be partially or fully cut off or otherwise removed from the matrix 150, or can be bent or folded and optionally tucked into the interproximal site. For example, such cutting or bending can be facilitated by providing the matrix material with corresponding intrinsic properties; for example, the intrinsic properties of the matrix material forming the handle element 163''' can differ chemically from the intrinsic properties of the matrix material forming the body portion 161'''. For example, one of the body portion 161''' or the handle element 163''' can include a polymer that is crosslinked or comprises stiffening fibers, while the other one of the body portion 161''' and the handle element 163''' will not be cross linked or will not have fibers, respectively.

Alternatively, for example, such cutting or bending can be facilitated by adding a substance to the handle element 163''' or to the body portion 161''' at a later stage, for example, after production, before or after placement of the matrix 150 in the interproximal site. For example, such a substance can include one or more of saliva, water, alcohol, cross linking agents, or enzymes. For example, such a substance can be configured to soften, or to harden, one of the handle element 163''' or the body portion 161''', compared to the other one of the handle element 163''' or the body portion 161'''.

Optionally, the precursor portion 160''' can be made from the same matrix material throughout, i.e., the handle element 163''' and the body portion 161''' are made from the same matrix material. Alternatively, the body portion 161''' is made from the matrix material, but the handle element 163''' is made from a different material—for example, the handle element 163''' is made from biodegradable material that degreased rapidly in the intraoral cavity, or that softens more easily than the body portion 161''' to allow the handle element 163''' to be manually packed into the interproximal site.

Optionally, the strip 100''' can be rolled a into a compact spiral form, and further optionally, the spirally-wound strip 100''' can be optionally enclosed in a dispensing box, for example as disclosed for the second example or third example, mutatis mutandis.

Figure 11A:
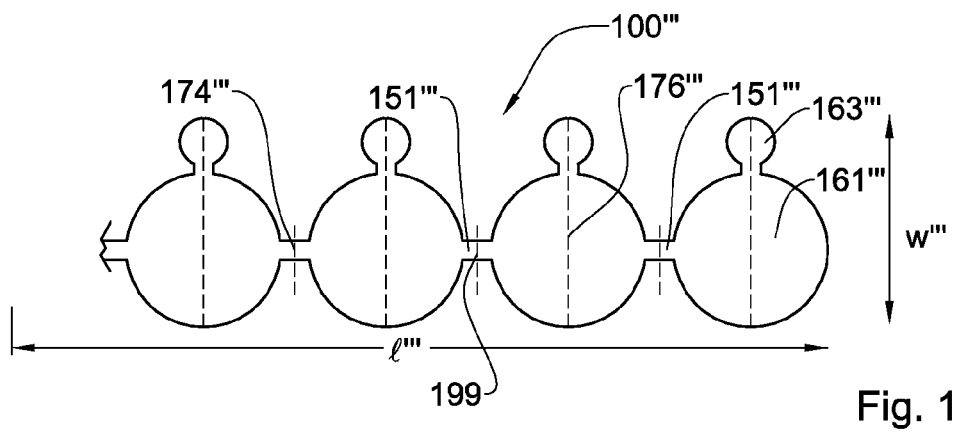
FIG. 11(a) illustrates in top view a fourth example of a substrate according to an aspect of the invention.

The example of the strip 100''' illustrated in FIG. 11(a) can be manufactured using similar methods to those directed at the first, second or third examples, or alternative variations thereof, mutatis mutandis.

The strip 100''' can be formed having separating facilitators 199 in the form of a first set of weakened lines, and optionally having a second set of weakened lines, for example as disclosed for the third example, mutatis mutandis. Thus, the first set of weakened lines comprises a plurality of first weakened lines 174''', which facilitate separation of the respective precursor portion 160''' from the remainder of the strip 100'''. Each first weakened line 174''' is provided at a respective tab 151''', along the width direction, and can comprise any suitable configuration to provide a weaker mechanical integrity than that of the precursor portions 160'''. For example, each first weakened line 174''' can comprise one or more of the following: a reduced thickness as compared to the thickness of the precursor portion 160'''; a plurality of perforations; a chemical agent that reduces the mechanical integrity of the matrix material; laser treatment to weaken or mark the line. For example, such chemicals agents can include one or more of: water, alcohol, enzymes, digestive chemicals, saliva, or other chemicals or mixtures thereof.

The second set of weakened lines comprises a plurality of second weakened lines 176''', which facilitate folding the respective matrix 150 thereat. In the illustrated example, a single second weakened line 176''' is provided at each respective precursor portion 160''', along the width direction and at the center of the precursor portion 160'''. However, other configurations are also possible. For example, a number of second weakened lines 176''' can be provided for each precursor portion 160''', allowing for the final matrix 150 to be folded about multiple fold lines. Additionally or alternatively, at least one second weakened line 176''' can be provided along a direction different from the width direction—for example along the length direction or obliquely thereto.

Figure 11B:
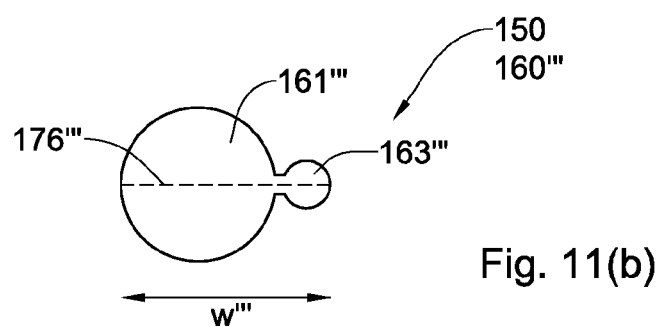
FIG. 11(b) illustrates in top view an example of a matrix obtained from the substrate of the example of FIG. 11(a)
Figure 11C:
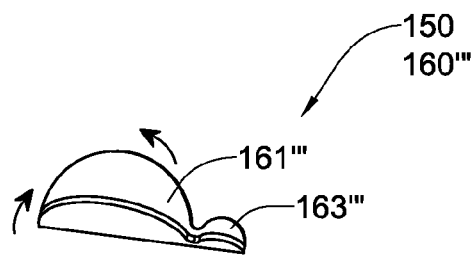
FIG. 11(c) illustrates the matrix of FIG. 11(b) in folded configuration.

For example, at least one second weakened line 176''' can be provided such as to divide the precursor portion 160''' in equal parts, for example as illustrated in FIGS. 11(b) and 11(c), and this weakened line 176''' generally bisects the body portion 161''' and the handle element 163'''. Thus, when folded about this weakened line 176''' the folded matrix 150, which is thus in the folded configuration, is symmetrical, and the handle element 163''' is also folded.

Alternatively, the weakened line 176''' divides the precursor portion 160''' into two unequal halves, with most or all of the handle element 163''' being found in the larger half. In such a case, when folded in the folded configuration the resulting matrix 150 is asymmetrical, and the handle element 163''' remains unfolded.

In any case, each second weakened line 176''' can comprise any suitable configuration to provide a weaker mechanical integrity than that of the precursor portions 160''. For example, each first weakened line 176''' can comprise one or more of the following: a reduced thickness as compared to the thickness of the precursor portion 160''; a plurality of perforations; a chemical agent that reduces the mechanical integrity of the matrix material; laser treatment to weaken or mark the line. For example, such chemicals agents can include one or more of: water, alcohol, enzymes, digestive chemicals, saliva, or other chemicals or mixtures thereof.

Alternatively, each second weakened line 176''' can have the same mechanical integrity as the remainder of the precursor portion 160''', and comprises instead a visual mark to guide the user to facilitate folding. Typically, the mechanical integrity of the second weakened lines 176''' is greater than that of the first weakened lines 174'''.

The example of the strip 100''' illustrated in FIGS. 11(a) and 11(b) can be manufactured using similar methods to those directed at the first and second examples, mutatis mutandis, to initially provide the strip 100''' with uniform thickness, and the strip 100'' can be subsequently processed to provide the plurality of first weakened lines 174''' and/or the plurality of second weakened lines 176'''. For example, this post-processing step can comprise chemically and/or physically treating the strip to provide the weakened lines.

Figure 10A:
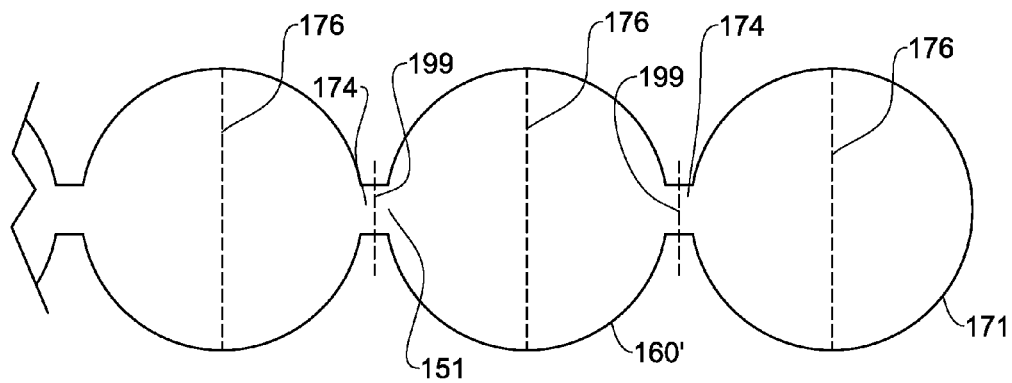
FIGS. 10(a) and 10(b) illustrate in top view and side view, respectively, a variation of the example of FIG. 9.
Figure 10B:
Figure 10I:
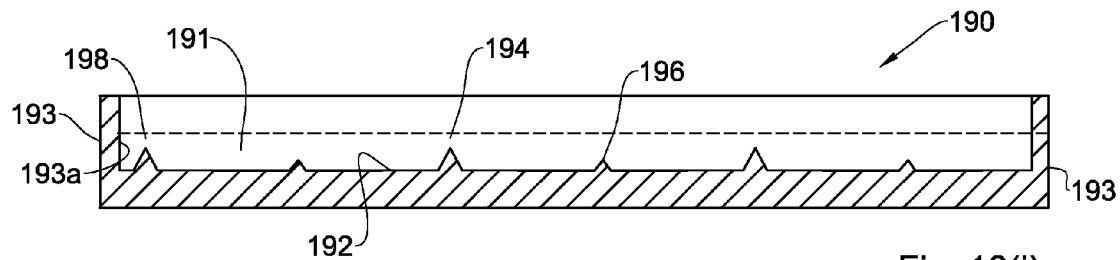
FIG. 10(i) illustrates an example of a mold useful for the manufacture of the substrate of FIGS. 10(a) and 10(b)
Figure 10E:
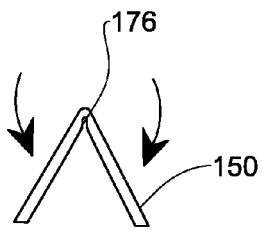
FIG. 10(e) illustrates the matrix of FIGS. 10(c) and 10(d) in folded configuration.
Figure 10C:
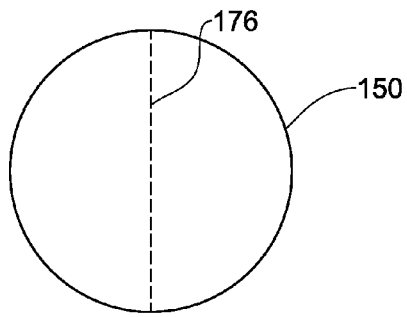
FIGS. 10(c) and 10(d) illustrate in top view and side view, respectively, an example of a matrix obtained from the substrate of the example of FIGS. 10(a) and 10(b)
Figure 10D:
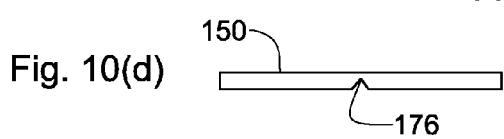
Figure 10H:
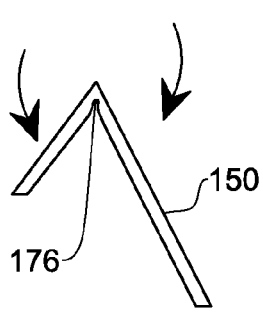
FIG. 10(h) illustrates the matrix of FIGS. 10(f) and 10(g) in folded configuration.
Figure 10F:
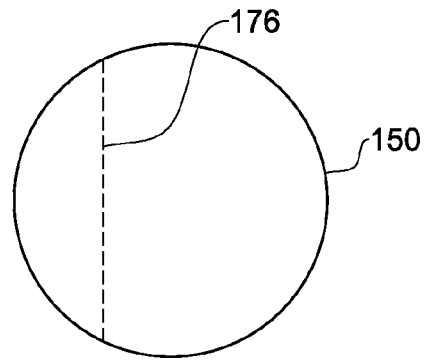
FIGS. 10(f) and 10(g) illustrate in top view and side view, respectively, another example of a matrix obtained from the substrate of the example of FIGS. 10(a) and 10(b)
Figure 10G:
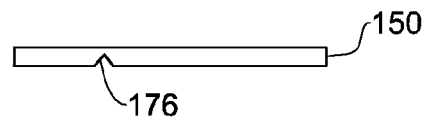
Figure 10J:
FIG. 10(j) illustrates in side view a variation of the example of the substrate of FIGS. 10(a) and 10(b)
Figure 10K:
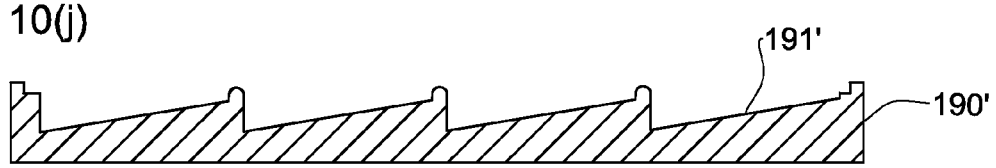
FIG. 10(k) illustrates an example of a mold useful for the manufacture of the substrate of FIG. 10(j)
Figure 10L:
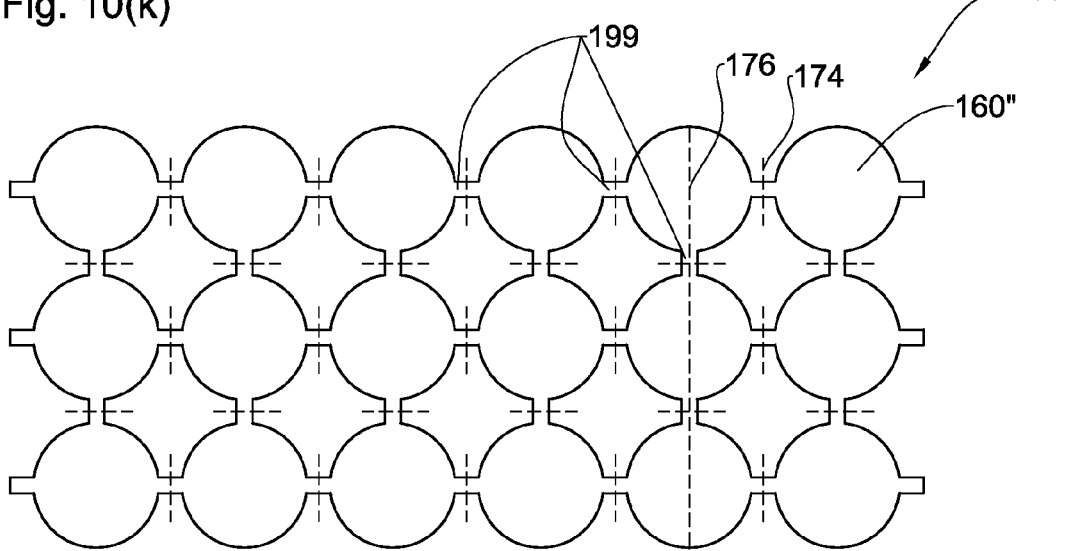
FIG. 10(l) illustrates in top view another variation of the example of the substrate of FIGS. 10(a) and 10(b).

Alternatively, the of the strip 100''' illustrated in FIGS. 11(a) and 11(b) can be manufactured using similar method to that disclosed for the alternative variation of the third example illustrated in FIGS. 10(b) and 10(i), mutatis mutandis, configured to ensure that the plurality of first weakened lines 174''' and/or the plurality of second weakened lines 176''' are integrally formed with the strip 100''. In such a case, the corresponding mold that is provided for casting the strip 100''' comprises a mold cavity that essentially complementary to the shape of the strip 100'''.

Figure 11D:
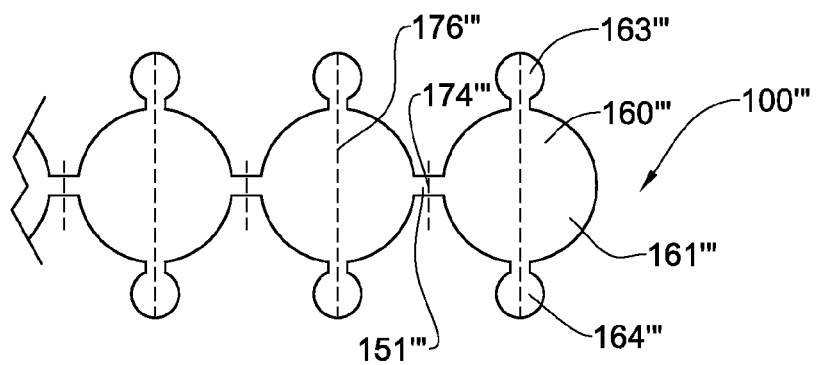
FIG. 11(d) illustrates in top view a variation of the example of FIG. 11(b).

In an alternative variation of the fourth example, and referring to FIG. 11(d), the precursor portion 160''' can optionally be provided with an additional handle portion 164''', in diametrically opposed relationship to handle portion 163'''. In yet other alternative variations of the fourth example, the precursor portion 160''' can optionally be provided with plurality of handle portions.

Figure 12A:
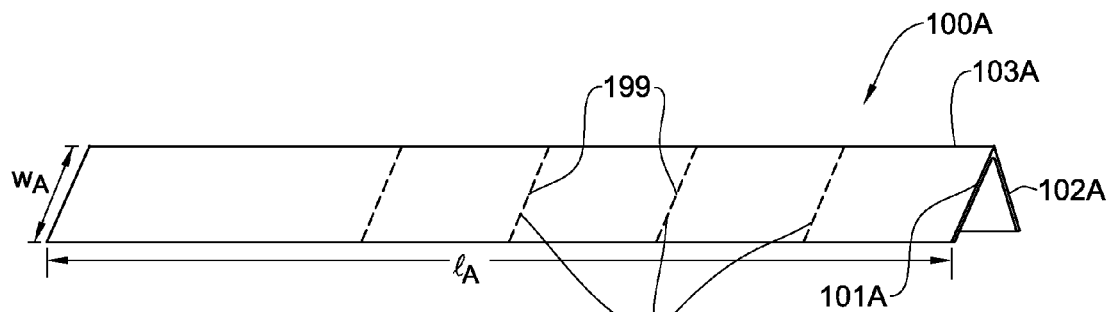
FIG. 12(a) illustrates in isometric view a fifth example of a substrate according to an aspect of the invention.
Figure 12B:
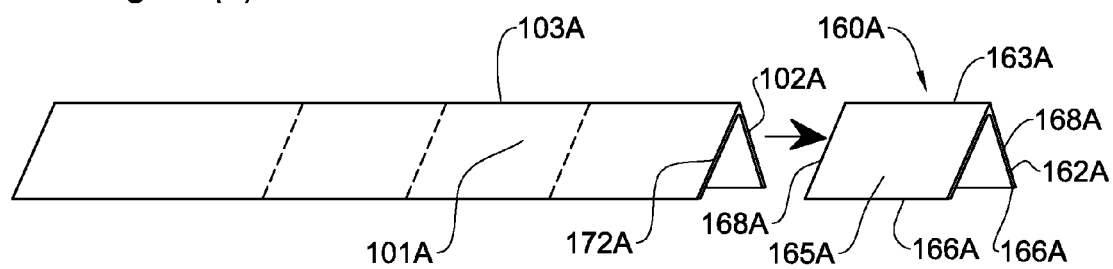
FIG. 12(b) illustrates in isometric view an example of a precursor portion being separated from the substrate of the example of FIG. 12(a)

In a fifth example, and referring to FIGS. 12(a) and 12(b), the substrate 100 is provided in the form of a continuous folded strip 100A, having a folded width $w_A$ and length $l_A$. In this example, the strip has a generally V-shaped cross-section, and comprises two parallel, generally rectangular sub-strips 101A, 102A joined at the apex 103A of the V, and the apex can be regarded as a fold line. Precursor portions $160_A$ of the strip having a width $w_A$ and any desired length up to length dimension $l_A$, and maintaining the V-shaped cross-section, can be separated from the strip $100_A$, for example by cutting or tearing off the precursor portion $160_A$. For example, such precursor portions $160_A$ have a pair of flaps $161_A$, $162_A$ joined together at the apex $163_A$ of the V, corresponding to sub-strips 101A, 102A and apex 103A.

Each flap $161_A$, $162_A$ has a respective free edge $166_A$ spaced from the apex $163_A$, and respective forward and aft edges $168_A$.

For example, such flaps $161_A$, $162_A$ can each be any desired repeatable shape, for example a parallelogram, or a square, or rectangular having an aspect ratio over 1.0, for example up to 2.0 or up to 3.0, or having an aspect ratio less than 1.0, for example 0.5 or 0.8.

Figure 12C:
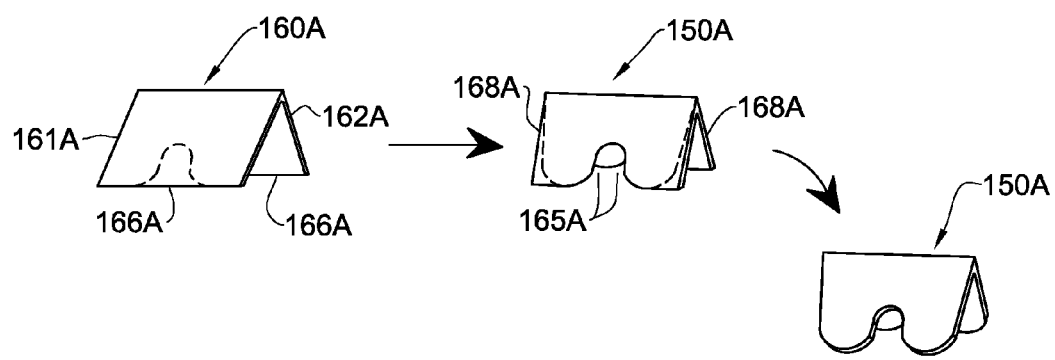
FIG. 12(c) illustrates an example of a matrix being formed from the precursor portion of FIG. 12(b)
Figure 12D:
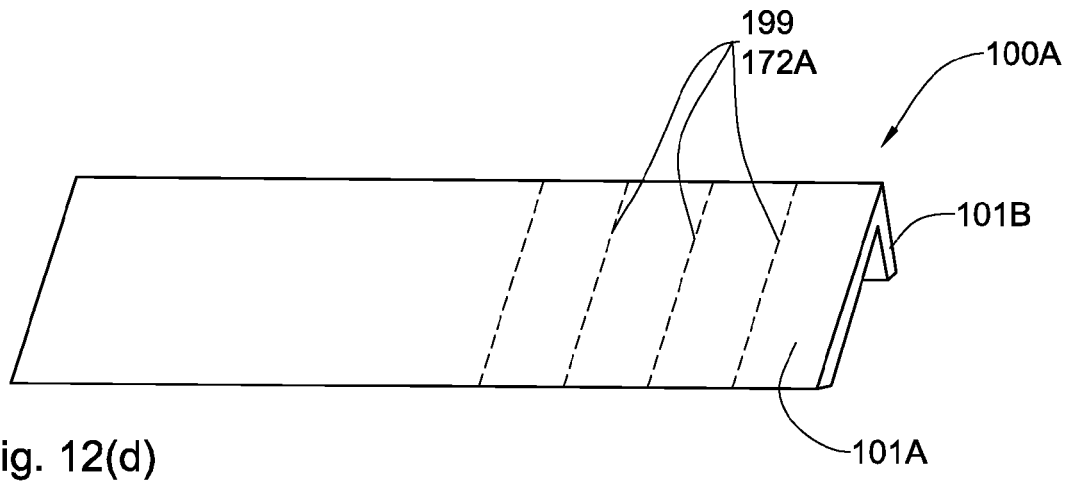
FIG. 12(d) illustrates in isometric view a variation of the example of FIG. 12(a)
Figures 12E, 12F:
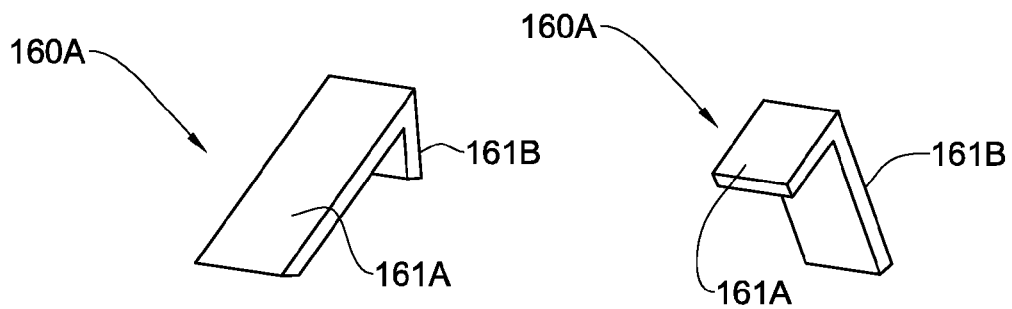
FIGS. 12(e) and 12(f) illustrate in isometric view alternative examples of a precursor portion obtained from the substrate of the example of FIG. 12(d)
Figure 12G:
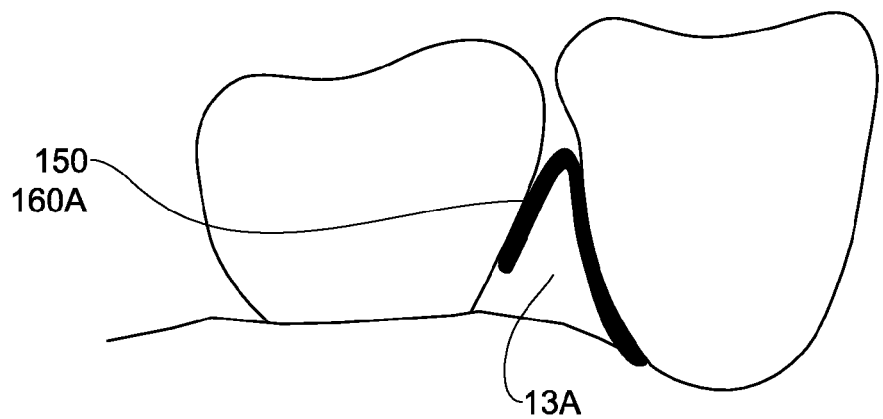
FIG. 12(g) illustrates in side view a matrix provided by the precursor portion of the example of FIG. 12(e) or 12(f) installed in an interproximal site.

In the example illustrated in FIGS. 12(a) to 12(c), the sub-strips 101A, 102A, are of similar size and shape to one another, and thus the strip 100A is symmetrical; similarly, flaps $161_A$, $162_A$ are of similar size and shape one to another, and thus respective precursor portion $160_A$ is also symmetrical. Alternatively, and as illustrated in FIGS. 12(d), 12(e) and 12(f), the sub-strips 101A, 102A, are of can be of different size and/or shape to one another. For example, sub strip 101A can have a larger width or a smaller width than sub strip 101B. Correspondingly, the flaps $161_A$, $162_A$ can be of different size and/or shape to one another, and thus the respective precursor portion $160_A$ is asymmetrical. For example, referring to FIG. 12(e) the flap $161_A$ can have a larger width than flap $162_B$, or, referring to FIG. 12(f) the flap $161_A$ can have a smaller width than flap $162_B$. Asymmetric matrices, corresponding to the asymmetric parts such as for example precursor portions $160_A$ illustrated in FIGS. 12(e) and 12(f), can be useful in an interproximal site 13A (see FIG. 12(g)) that is correspondingly asymmetrical, for example having a gum pathology in which the gum is more receded in one tooth than in its adjacent tooth.

In any case, and to facilitate identifying and/or separating each precursor portion $160_A$ serially from the strip $100_A$, the strip $100_A$ can be marked at intervals with separating facilitators 199 in the form of lines $172_A$, in which the spacing between adjacent pairs of lines $172_A$ corresponds to the desired width for the respective precursor portion $160_A$. The lines $172_A$ can be etched, engraved, or otherwise formed including a physical weakness along which it is easier to fold and cut the strip $100_A$, or can be formed as an optical mark, for example having a color and/or contrast different from the remainder of the strip $100_A$.

After the precursor portion $160_A$ is separated from the strip $100_A$, it can be cut further and reshaped as desired to provide the matrix 150. For example precursor portion $160_A$ can be shaped in the form of matrix $150_A$ illustrated in FIG. 12(c) by cutting a concave indentation $165_A$ in each of the flaps $161_A$, $162_A$ at the respective free edges $166_A$ thereof. Optionally, the matrix $150_A$ can be further shaped, for example by curving the fore and aft edges $168_A$ as illustrated in FIG. 12(c) to form reshaped matrix $150_{A'}$, which corresponds to the folded matrix 20' of FIGS. 2(a) to 2(f), for example.

In this example, the sub-strips 101A, 102A (and thus flaps $161_A$, $162_A$) are each of uniform thickness throughout.

For example, the folded strip $100_A$ can be manufactured by first manufacturing an unfolded strip, for example as disclosed above for the example of FIG. 7 or 8. Then the unfolded strip is removed from the mold, and subsequently folded to provide the folded strip $100_A$. Alternatively, the unfolded flat strip is placed in a warm and/or humid environment, the strip being draped over a wedge-shaped projection having an apex corresponding to the desired apex of the folded strip. When the strip is fully abutting the wedge, the strip is allowed to dry.

Figure 13A:
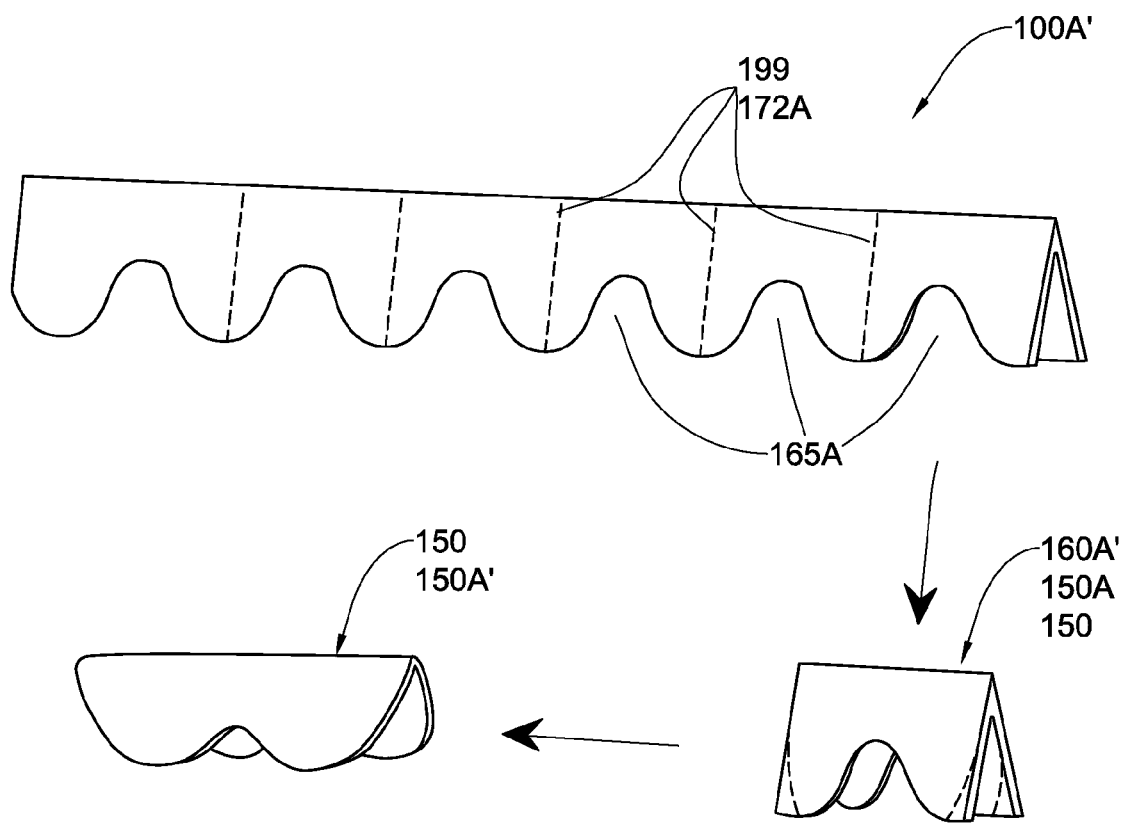
FIG. 13(a) illustrates in isometric view a variation of the substrate example of FIG. 12(a), with a precursor portion being separated from the substrate, and a matrix being formed from the precursor portion.
Figure 13B:
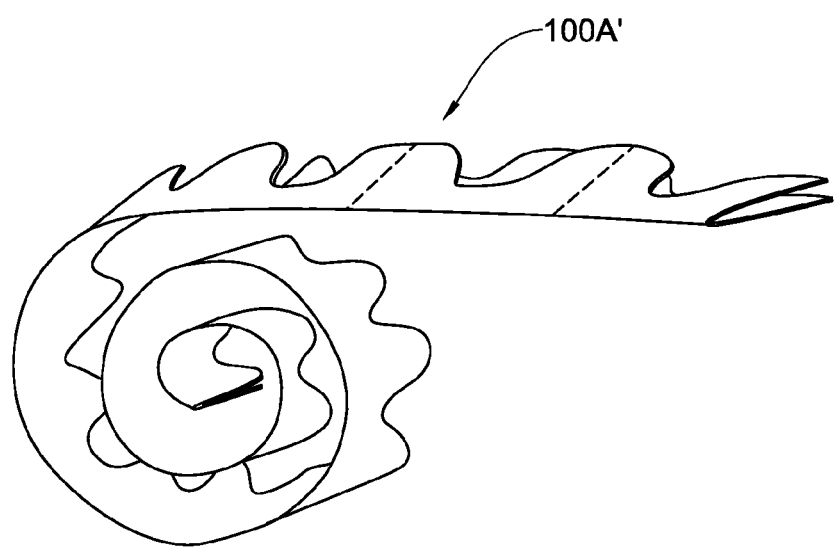
FIG. 13(b) illustrates in isometric view the substrate example of FIG. 13(a) in spiral wound configuration.
Figure 13C:
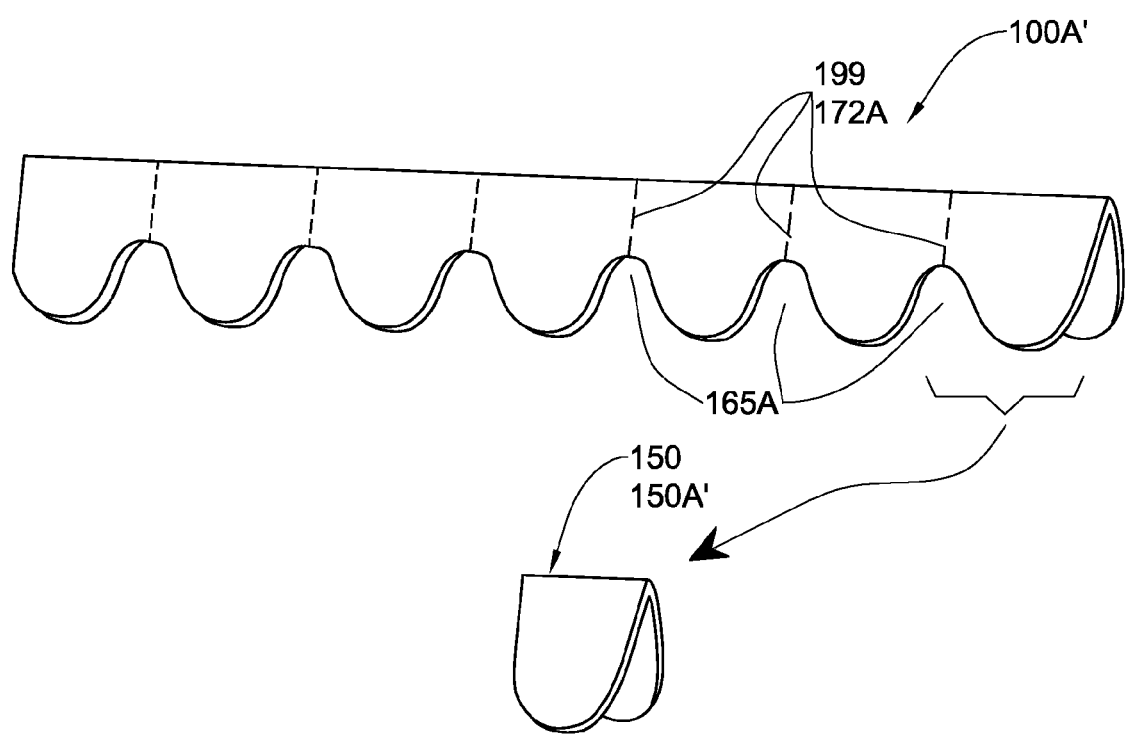
FIG. 13(c) illustrates in isometric view another variation of the substrate example of FIG. 12(a), with a precursor portion being separated from the substrate and forming a matrix.

In an alternative variation of the fifth example, and referring to FIGS. 13(a) and 13(b), the strip $100_{A'}$ is formed, corresponding to strip $100_A$, mutatis mutandis, but with the indentations $165_A$ integrally formed between adjacent pairs of separating facilitators 199, which are in the form of lines $172_A$. Thus, the precursor portion $160_{A'}$ that is separated from the strip $100_A$ is already in the form of matrix $150_A$ of FIG. 11(c), and optionally this can be further shaped, for example by curving the fore and aft edges $168_A$ as illustrated in FIG. 13(a) to form reshaped matrix $150_{A'}$, which again corresponds to the folded matrix 20' of FIGS. 2(a) to 2(f). In this example, the separating facilitators 199, which are in the form of lines $172_A$, are provided along the widest width of the strip $100_{A'}$. Alternatively, and as illustrated in FIG. 13(c), the separating facilitators 199, which are in the form of lines $172_A$, can instead be provided along the narrowest width of the strip $100_{A'}$, to produce a circular or oval shaped matrix $150_{A'}$, for example.

As illustrated in FIG. 13(b), the folded strip $100_{A'}$ can be rolled along the length direction (i.e., about an axis parallel to the width direction) into a compact spiral form, and optionally the spirally-wound strip $100_{A'}$ can be optionally enclosed in a dispensing box, for example as disclosed above for the first example, mutatis mutandis. Similarly, such a box can be used as a dispenser, in which precursor portions $160_{A'}$ of the strip can be serially removed by extracting the leading edge of the strip $100_{A'}$ through the opening of the box and then cutting off the desired length of strip $100_{A'}$. Thus, the matrix $150_A$ or $150_{A'}$ is initially in a folded form, i.e., in the folded configuration, prior to being separated from the strip $100_{A'}$.

In a similar manner, mutatis mutandis, strip $100_A$ of FIG. 12(a) can also be can be rolled into a compact spiral form, enclosed in a dispensing box, and the respective precursor portion $160_A$ dispensed therefrom.

Figure 14A:
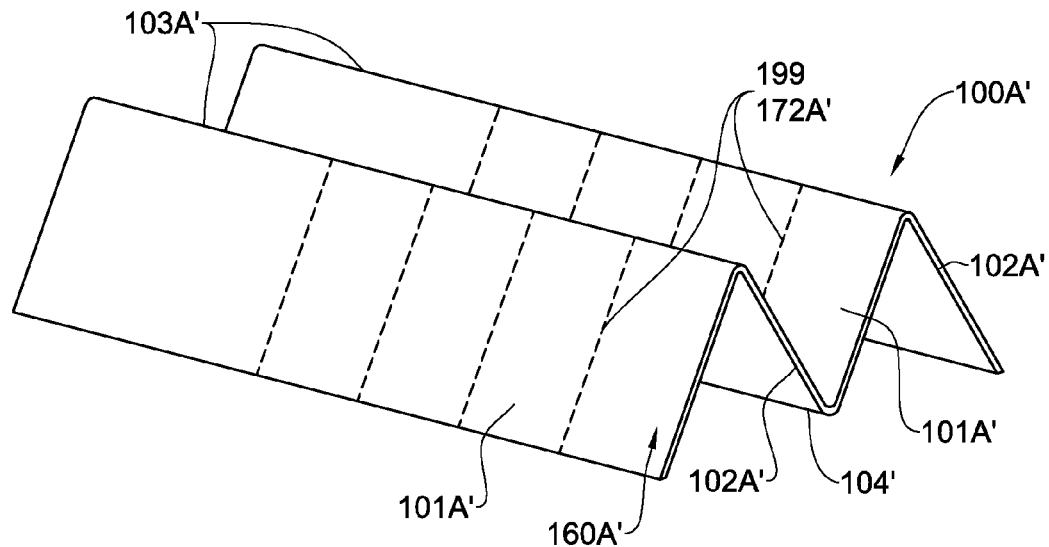
FIG. 14(a) illustrates in isometric view another variation of the substrate example of FIG. 12(a)
Figure 14B:
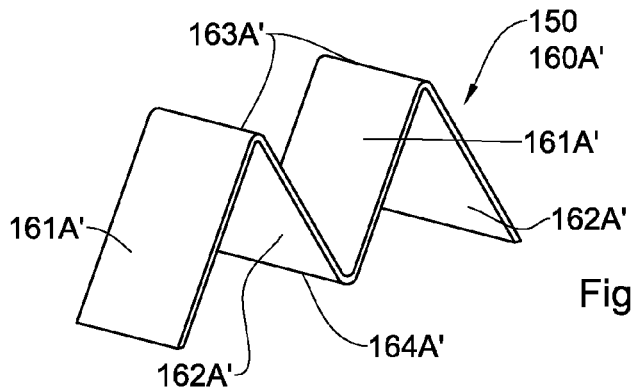
FIG. 14(b) illustrates in isometric view a precursor portion obtained from the substrate example of FIG. 14(a)
Figure 14C:
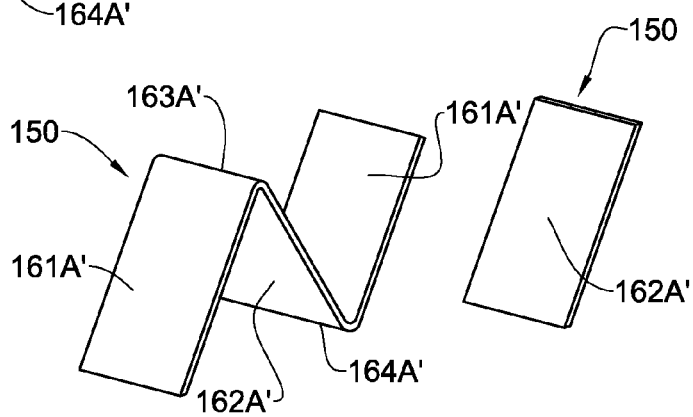
FIG. 14(c) illustrates in isometric view a matrix being formed from the precursor portion of the example of FIG. 14(b)

An alternative variation of the fifth example, illustrated in FIGS. 14(a) to 14(c), comprises all the features and elements of the fifth example that is illustrated in FIGS. 12(a) to 13(b), mutatis mutandis, but with some differences, as will become clearer herein. In the example of FIGS. 14(a) to 14(c), the substrate 100 is provided in the form of a continuous folded strip 100A', having a folded width $w_A$ and length $l_A$, but having more than two sub-strips longitudinally joined to one another in accordion-like cross-section, rather than the two sub-strips of the examples of FIGS. 12(a) to 13(b). In this example, the strip 100A' has a generally W-shaped cross-section, and comprises two pairs of parallel, generally rectangular sub-strips 101A', 102A' joined at an apex 103A' to form a V-shaped cross-section, and the two pairs of sub-strips 101A', 102A' are joined to one another via a common apex 104A" to provide the W-shaped cross section for the strip 100A'. Thus, each pair of sub-strips 101A', 102A' together with its respective apex 103A' is similar to the strip 100A of examples of FIGS. 12(a) to 13(b), mutatis mutandis.

The two apices 103A' and the middle apex 104A' can each be regarded as a fold line. Precursor portions $160_{A'}$ of the strip having a width $w_A$ and any desired length up to length dimension $l_A$, and maintaining the W-shaped cross-section, can be separated from the strip $100_A$ (for example in a similar manner to that disclosed for the examples of FIGS. 12(a) to 13(b), mutatis mutandis), for example at separating facilitators 199 in the form of lines $172_{A'}$, and thus each such precursor portions $160_{A'}$ comprises two pairs of flaps $161_{A'}$, $162_{A'}$ joined together at the two outer apices $163_{A'}$ and the middle apex $164_{A'}$ of the W, corresponding to two pairs of sub-strips 101A', 102A' and apices 103A' and 104A'.

Referring to FIG. 14(b), the W-shaped precursor portion $160_{A'}$ can constitute the matrix 150, or can be trimmed further as desired to provide the appropriately shaped matrix 150. Such a W-shaped precursor portion $160_{A'}$ can be of particular use in situations where the interproximal site of a patient is large, and a regular V-shaped matrix having flaps of similar thickness is not sufficiently thick.

Alternatively, and referring to FIG. 14(c) and FIG. 4(d), the W-shaped precursor portion $160_{A'}$ can be trimmed further as desired to provide the appropriately shaped matrix 150. For example, and referring to FIG. 14(c), the W-shaped precursor portion $160_{A'}$ can be trimmed by cutting at one of the apices 103A', to provide a three-layered matrix 150 having three flaps $161_{A''}$, $162_{A''}$, $161_{A''}$, joined at the respective apices 103A' and 104A', and concurrently providing a separate matrix 150 in the form of a single flap $161_{A''}$. In another example, and referring to FIG. 14(d), the W-shaped precursor portion $160_{A'}$ can be trimmed by cutting at apex 104A', to provide a pair of two-layered matrices 150, each having two flaps $161_{A''}$, $162_{A''}$, joined at the respective apex 103'

Figure 14D:
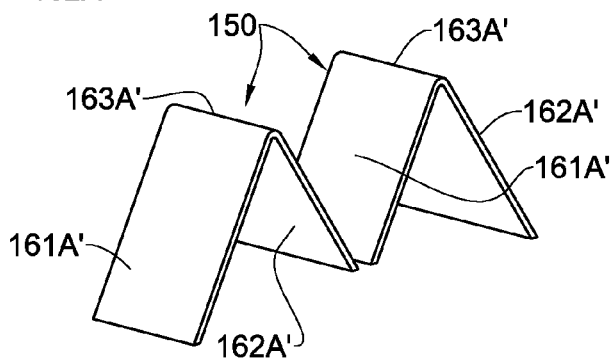
FIG. 14(d) illustrates in isometric view another matrix being formed from the precursor portion of the example of FIG. 14(b).

Each of the matrices 150 of the above examples, illustrated in FIGS. 14(b) to 14(d), can be trimmed further, for example by trimming the edges in a similar manner to the matrices illustrated in FIG. 12(c) or FIG. 13(a), mutatis mutandis.

Figure 15A:
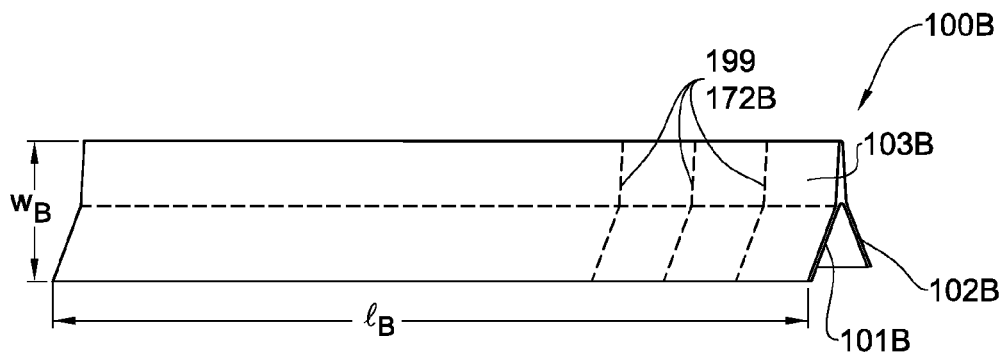
FIG. 15(a) illustrates in isometric view a sixth example of a substrate according to an aspect of the invention.
Figure 15B:
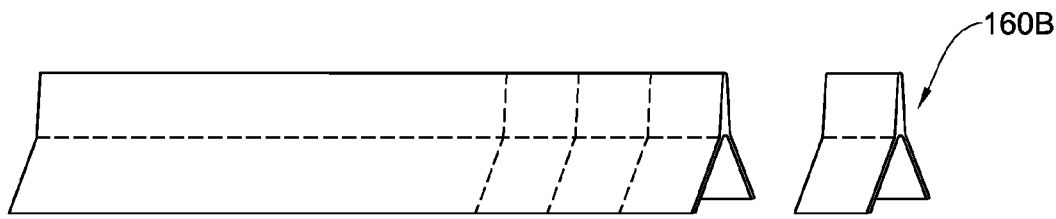
FIG. 15(b) illustrates in isometric view an example of a precursor portion being separated from the substrate of the example of FIG. 15(a)
Figure 15C:
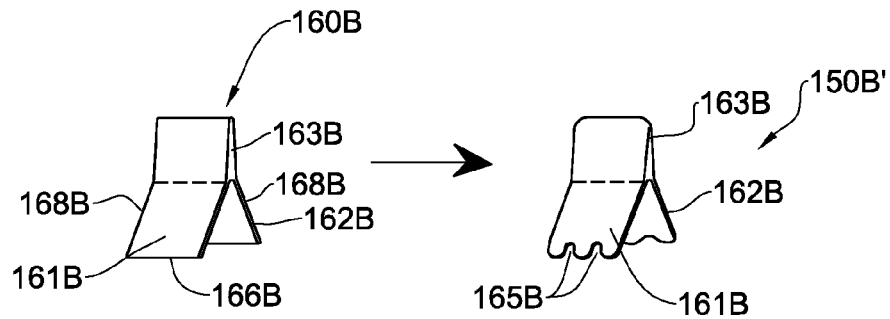
FIG. 15(c) illustrates an example of a matrix being formed from the precursor portion of FIG. 15(b)

In a sixth example, and referring to FIGS. 15(a), 15(b) and 15(c), the substrate 100 is provided in the form of a continuous partially folded strip 100B, having a folded width $w_B$ and length $l_B$. In this example, the strip has a generally Y-shaped cross-section, and comprises two parallel, generally rectangular sub-strips 101B, 102B joined to elongated portion 103B corresponding to the lower arm of the Y. Precursor portions 160B of the strip having a width $w_B$ and any desired length up to length dimension $l_B$, and maintaining the Y-shaped cross-section, can be separated from the strip $100_B$, for example by cutting or tearing off the precursor portion $160_B$. For example, such precursor portions $160_B$ have a pair of flaps $161_B$, $162_B$ joined together at one end of the elongated precursor portion $163_B$ of the Y, corresponding to sub-strips 101B, 102B and elongated portion 103B. Each flap flaps $161_B$, $162_B$ has a respective free edge $166_B$ spaced from the elongated portion $163_B$, and respective forward and aft edges $168_B$.

For example, such flaps $161_B$, $162_B$ and the elongated portion $163_B$ can each be of any suitable shape, for example parallelogram, square, or rectangular, for example having an aspect ratio over 1.0, for example up to 2.0 or up to 3.0, or having an aspect ratio less than 1.0, for example 0.5 or 0.8. To facilitate identifying and/or separating each precursor portion 160B serially from the strip $100_B$, the strip 100B can be marked at intervals with separating facilitators 199 in the form of lines $172_B$, in which the spacing between adjacent pairs of lines $172_B$ corresponds to the desired width for the respective precursor portion $160_B$. The lines 172E can be etched, engraved, or otherwise formed including a physical weakness along which it is easier to fold and cut the strip $100_B$, or can be formed as an optical mark, for example having a color and/or contrast different from the remainder of the strip $100_B$.

After the precursor portion $160_B$ is separated from the strip $100_B$, it can be cut or trimmed further and reshaped as desired to provide the matrix 150. For example precursor portion $160_B$ can be shaped in the form of matrix 150B illustrated in FIG. 15(c) by cutting concave indentations 165E in each of the flaps $161_B$, $162_B$ at the respective free edges $166_B$ thereof. Optionally, the matrix $150_B$ can be further shaped, for example by curving the fore and aft edges $168_B$, as well as free edges $166_B$ to provide a wavy edge, as illustrated in FIG. 15(c) to form reshaped matrix $150_{B''}$, for example corresponding to the Y-shaped matrix or retention device 50 of FIGS. 5(a) to 5(d).

In this example, the sub-strips 101B, 102B, and elongated portion 103B (and thus flaps $161_B$, $162_B$ and the elongated portion $163_B$) are each of uniform thickness throughout. Alternatively, each of the sub-strips 101B, 102B can be of a different thickness to that of elongated portion 103B.

Figure 15D:
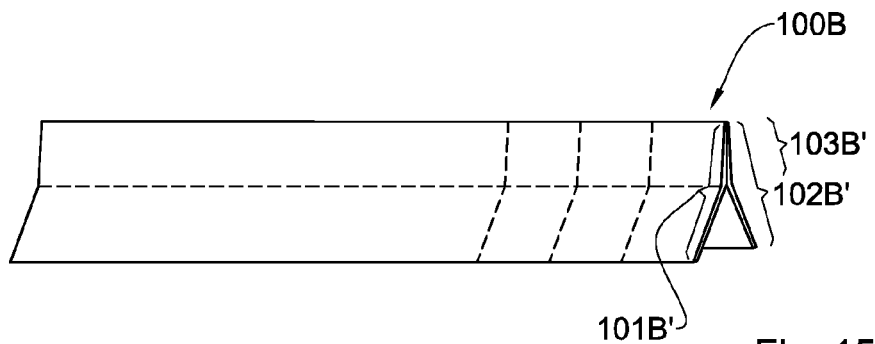
FIG. 15(d) illustrates in isometric view a variation of the example of FIG. 15(a).

Optionally, and referring to FIG. 15(d), the Y-shaped strip 100B can be formed by superposing two sub-strips 101B', 102B', and joining the two strips together at one side of the sub-strips 101B', 102B' to form the elongated portion 103B'. For example, the two sub-strips 101B', 102B', (for example in the form of long or short rectangular strips, for example approximately between 30-200 microns thick) are produced in a manner similar to that disclosed above, mutatis mutandis. Then, a longitudinal portion (for example between 20% and 80%) of both sub-strips 101B', 102B', and joining the two strips together at one side of the sub-strips 101B' are hydrated and then merged under pressure (for example compressed together), followed by drying to form the elongated portion 103B, while concurrently the remaining portions of both sub-strips 101B', 102B' are kept apart and at an appropriate angle (for example, between about 20° and 50°) during the drying process, for example using an appropriate wedge-shaped separator therebetween.

Alternatively, the Y-shaped strip $100_B$ can be integrally formed using a mold having a mold cavity complementary in shape to that of the Y-shaped strip $100_B$.

In an alternative variation of the sixth example, the indentations $165_B$ are integrally formed between adjacent pairs of lines $172_B$.

The Y-shaped strip 100B of the examples of FIGS. 15(a) to 15(d), or alternative variations of these examples, can be rolled along the length direction (i.e., about an axis parallel to the width direction) into a compact spiral form, and optionally the spirally-wound Y-shaped strip can be enclosed in a dispensing box, for example as disclosed above for the first example, mutatis mutandis. Similarly, such a box can be used as a dispenser, in which precursor portions $160_B$ of the strip can be serially removed by extracting the leading edge of the strip $100_B$ through the opening of the box and then cutting off the desired length of strip $100_B$. Thus, the matrix $150_B$, is initially Y-shaped prior to being separated from the strip $100_{A''}$.

The above or other examples of matrices 150 (or the precursor respective precursor portions from which the matrix is formed) having a so-called "folded" configuration can be further manipulated in a variety of ways to provide many different configurations that are useful for implantation in the intra oral cavity of a patient, in particular an interproximal site. In this folded configuration, at least two flaps are superposed one on the other, partially or fully, and joined together at an edge. Thus, the matrix 150 or its respective precursor portion can be initially formed as a flat portion of matrix material that is subsequently folded about a fold line to provide the folded configuration, or, the matrix 150 can be formed directly (or via the respective precursor portion) in the folded configuration without any actual initial folding being carried out. An example of such a matrix 150 formed from a precursor portion 160X in the folded configuration is illustrated in FIG. 16(a), comprising two flaps 161X, 162X are superposed one on the other, and joined together at an apex or edge 163X. Each flap 161X, 162X has a respective free edge 166X spaced from the apex 163X, and respective forward and aft edges 168X. Thus, precursor portion 160X can correspond to, or is included in, the precursor portions illustrated in FIGS. 7(a) to 15(d), for example.

The precursor portion 160X can be further manipulated as shown in FIG. 16(b) by inwardly curling the free ends of the flaps 161X, 162X to provide the required matrix 150. For example, such a configuration for matrix 150 can be useful for a number of applications, for example: in large furcations and interproximal spaces of adjacent teeth, for example where significant gingival and periodontal recession has occurred; for are of a size and shape appropriate for receiving the respectively sized and shaped matrix 150.

Alternatively, the precursor portion 160X can be further manipulated as shown in FIG. 16(c) by concurrently curving the flaps 161X, 162X to provide the required matrix 150 in curvate form. For example, such a configuration for matrix 150 can be useful for a number of applications, for example: in large furcations and interproximal spaces of adjacent teeth, for example where significant gingival and periodontal recession has occurred; for are of a size and shape appropriate for receiving the respectively sized and shaped matrix 150.

Alternatively, the precursor portion 160X can be further manipulated as shown in FIG. 16(c) by rolling the flaps 161X, 162X together to provide the required matrix 150 in rolled configuration. For example, such a rolled configuration for matrix 150 can be useful for physically affixing in a furcation (33) using a tweezers, for example similar to rolled device HH physically fixed in the furcation (33) of the molar illustrated in. FIG. 3b, mutatis mutandis.

Figure 17A:
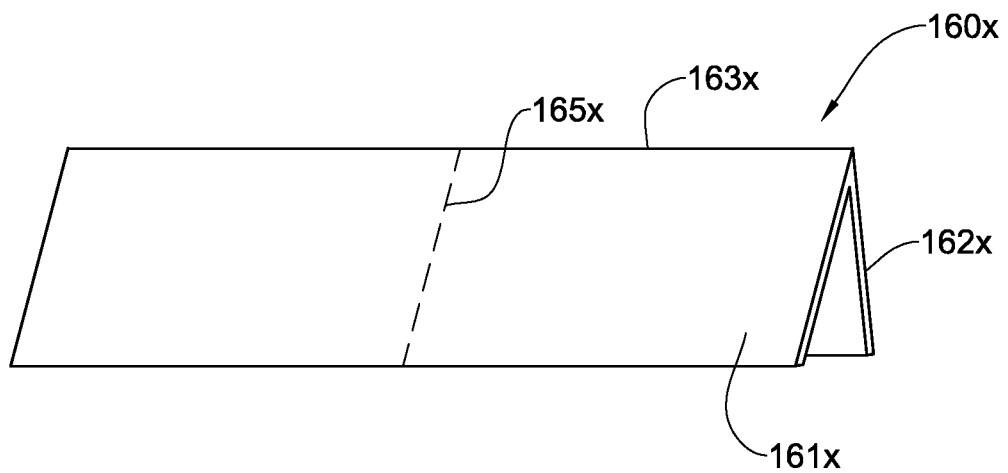
FIG. 17(a) illustrates in isometric view an alternative variation of the example of the precursor portion of FIG. 16(a)
Figure 17B:
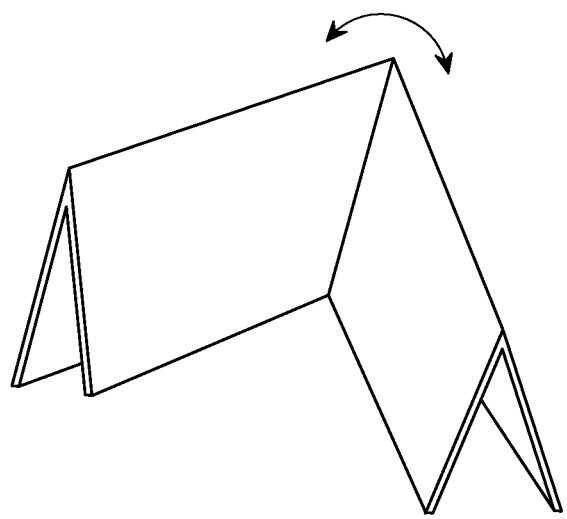
FIGS. 17(b), 17(c), illustrate in isometric view the matrix of FIG. 17(a) manipulated into alternative forms.
Figure 17C:
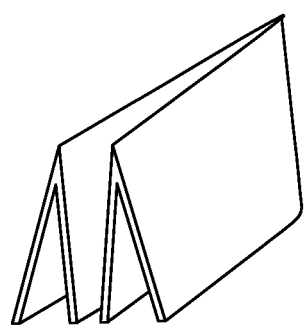

Alternatively, the precursor portion 160X can be further manipulated as shown in FIGS. 17(a) to 17(c) by folding the flaps 161X, 162X over themselves, for example about a fold line 165X, which can be for example generally orthogonal to edge 163X. in this manner, the resulting matrix 150 has effectively four layers of flaps superposed over one another. For example, such a configuration for matrix 150 can be useful for a number of applications, for example: in large furcations and interproximal spaces of adjacent teeth, for example where significant gingival and periodontal recession has occurred; for are of a size and shape appropriate for receiving the respectively sized and shaped matrix 150.

The matrix 150 (and also the corresponding precursor portion) for any of the above examples and alternative variations thereof, can further comprise stiffening elements embedded therein. For example, such stiffening elements can be useful for facilitating manipulation and insertion of a matrix in folded configuration into an interproximal site. Additionally or alternatively, such stiffening elements can be useful for preventing or minimizing bending of the matrix along other fold lines.

Figure 18A:
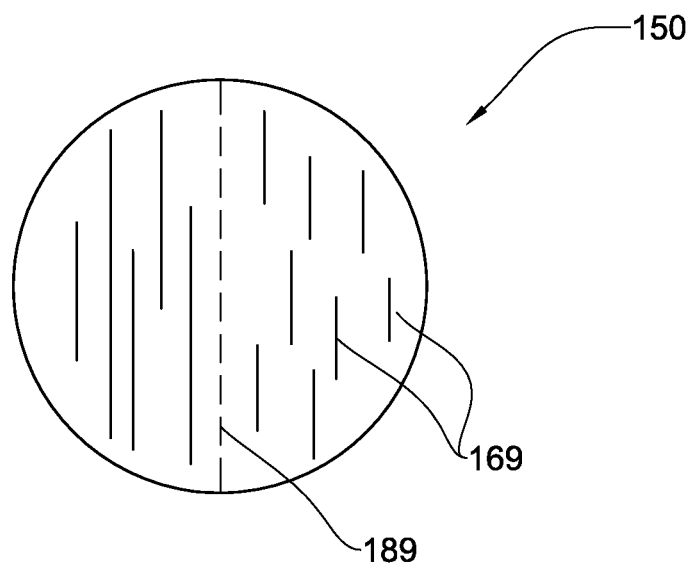
FIGS. 18(a) and 18(b) illustrate in top view and side view, respectively, another variation of the example of a matrix including stiffening elements.
Figure 18B:
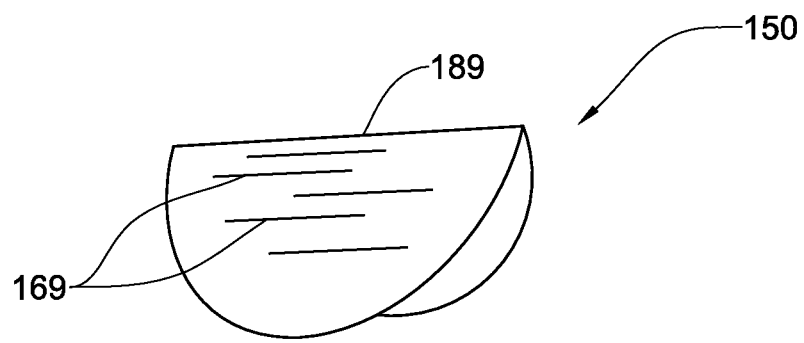

Referring to FIGS. 18(a) and 18(b), a typical matrix 150 (which for example can be the matrix according to any one of the above examples of the matrix or its precursor portion, or alternative variations thereof, mutatis mutandis) comprises such stiffening elements in the form of a plurality of fibers 169. In this example at least a majority of the plurality of fibers 169 are arranged in generally parallel relationship with the "fold line" 189 of the matrix 150, wherein the fold line 189 corresponds to the apex between the two flaps of the matrix 150. By generally parallel relationship is meant that such fibers can be at an angle of up to +45° to the fold line 189, preferably at an angle of up to ±30° to the fold line 189, more preferably at an angle of up to ±15° to the fold line 189, more preferably at an angle of up to ±50 to the fold line 189.

In at least the above examples, such fibers 169 do not cross fold line 189, and/or indeed such fibers 169 do not cross any separation line that may be formed between adjacent said matrices 150.

Alternatively, the fibers 169 can be randomly aligned in the matrix 150.

Alternatively, the fibers 169 can aligned in two or more parallel groups to form various ordered mesh-like alignments. Such alignments can be uniform or restricted to specific areas (e.g. excluded from the cutting bending/folding areas, where such areas are found in the matrix 150 or its precursor portion).

For example, such fibers 169 can include one or more of or made from: glass fibers (within or without for example polyester resin), carbon fibers (within or without for example epoxy resin), natural silk fibers, silicon carbide and nitride, boron, alumina ($Al_2O_3$), synthetic polymers (for example poly(methyl) methacrylate, poly(methyl methacrylate), poly(methacrylic acid), polystyrene, polycarbonates) and tin chains.

For example, the fibers 169 can be bound to the matrix (e.g. cross linked) or can be unbound within the matrix.

Figure 19A:
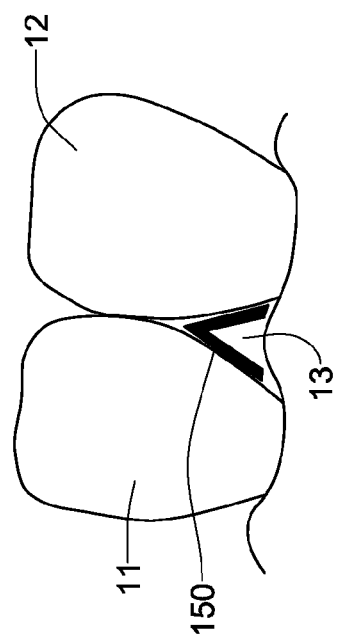
FIG. 19(a) illustrates in side view an example of a folded matrix accommodated in an interproximal space.
Figure 19B:
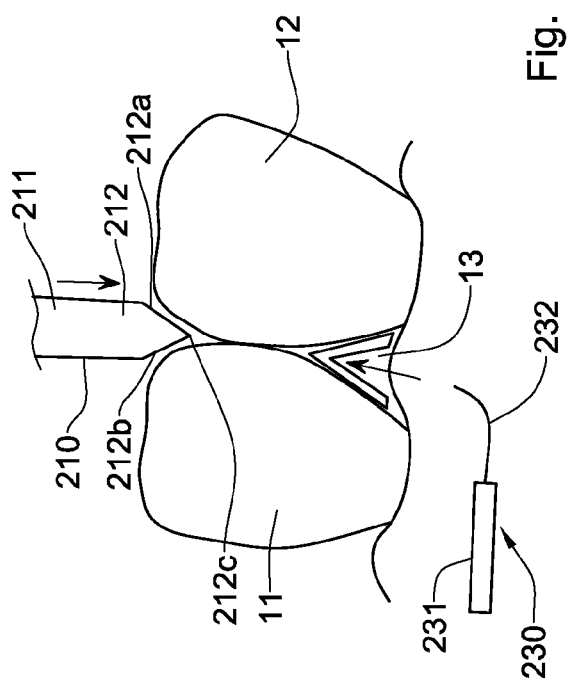
FIG. 19(b) illustrates in side view an example of a wedge member being used for assisting positioning of the folded matrix of FIG. 19(a) in the interproximal space.
Figure 19C:
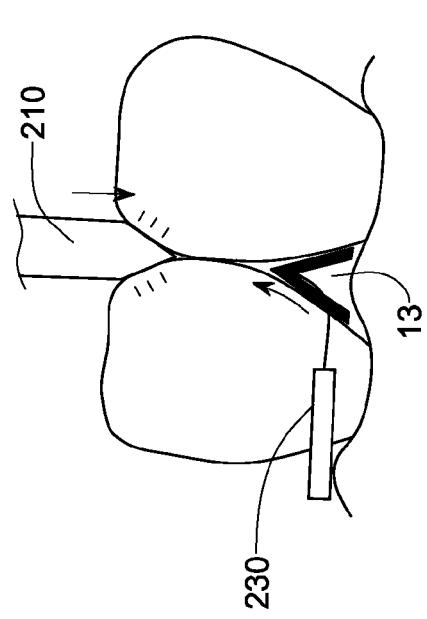
FIG. 19(c) illustrates in side view an example of a tool being used for further assisting positioning of the folded matrix of FIG. 19(a) in the interproximal space.
Figure 19D:
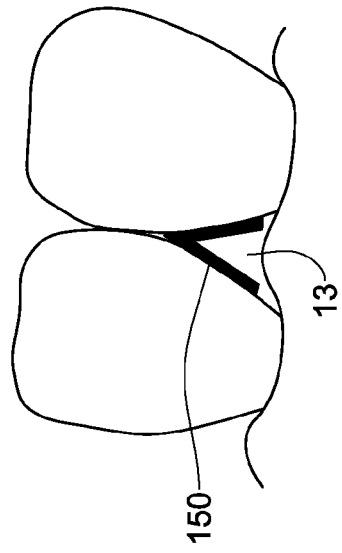
FIG. 19(d) illustrates in side view the folded matrix of FIG. 19(a) further wedged in the interproximal space

In the above first to sixth examples or alternative variations thereof, and referring also to FIG. 19(a), the respective matrix 150 in folded configuration can be inserted into the interproximal site 13, for example using any of the methods disclosed above for the examples illustrated in FIGS. 1(a) to 5(d), mutatis mutandis. Optionally, to facilitate placement of the matrix, for example where direct access into interproximal site is difficult, or where the adjacent teeth 11, 12 are in very tight contact, the insertion process can at least in some cases be facilitated using a wedging device. Referring to FIG. 19(b), an example of such a wedging device 210 is in the form of a tool having a handle 211 at a proximal end and a wedge member 212 at a distal end. The wedge member 212 has two opposed surfaces 212a, 212b, diverging from one another from the distal edge 212c. In use, the wedge member 212 is pushed inbetween the teeth 11, 12 in an apical direction, such that surfaces 212a, 212b temporarily and partially separate the teeth 11, 12, facilitating insertion of the matrix 150 into the interproximal site 13. Optionally, and referring to FIG. 19(b), a second tool 230, having a proximal handle 231 and a distal probe or hook element 232 can be used to reposition the matrix 150, either when in situ in the interproximal site 13, or concurrently while inserting the matrix 150 into the interproximal site 13 when using the wedging device 210. For example, and referring to FIG. 19(c), the tool 230 can be manipulated so that the hook element 232 is inserted between the superposed flaps of the matrix 150, and the hook element 232 can then be used to urge the matrix in the apical direction to further wedge the matrix 150 in the interproximal space 13, as illustrated in FIG. 19(d).

The above embodiments and examples, and their applications are not limited to devices of a biodegradable, resorbable or non-resorbable nature nor any combination thereof which are left in situ, but include devices that are activated or influenced by external means such as chemical or physical intervention. This forms a tough solid device at the site. An example of a physical application such as laser irradiation using $CO_2$ lasers, Nd:YAG lasers and Argon lasers.

The physical affixing of the device of the present invention is by way of a physical property of the matrix, in particular wherein the matrix comprises a hydrophilic polymer which softens and swells in situ by the hydration thereof in the oral cavity after accommodation at the dental site. The expansion can be designed to thicken (e.g. to 250%) in size substantially more than it elongates (e.g. 20%), thereby not extruding excessively out of the interproximal and tooth domain. Optionally, the retention device comprises at least one adhesive surface or part thereof such as to enable the system to adhere or be fixed at a dental site.

Again, of course this invention is not limited to the above-described embodiments or examples, but encompasses all the variations thereof. It is also evident to those schooled in the art that general toxicity, allergic responses and pulp responses need to be investigated prior to applying the proposed techniques clinically.

In the system according to the present invention, the oral activity provided by the active material or materials may be medical treatment such as fluoridization, remineralization or mineralization and desensitization and/or aesthetic treatment such as tooth whitening or providing breath fresheners, and/or any other desired activity.

Thus, the different components of the matrix of the invention, in particular according to the above embodiments, examples, and alternative variations thereof, can comprise a range of chemicals with the following functions:

The Primary Active Fluoridating Mineralization and/or Remineralization Agents

The fluoride releasing agent/s and other mineralizing and remineralizing agent/s can be embedded within the polymeric matrix or matrices of the invention, and released from there in a controlled or sustained manner with or without at least one auxiliary chemical or physical step for example electrodes, sonification or laser application to the device in situ. The matrix or matrices described in this invention can comprise at least one primary active fluoridizing mineralization and/or remineralization agent which provides fluoride and/or other ions, which primary agents can be divided into fluoridating agents and other mineralizing and/or remineralizing agents.

Fluoridation Agents

This agent can be any single or any combination of inorganic or organic fluoride-containing pharmaceutically acceptable chemicals known or to be developed. These include, but are not limited to amine fluorides, e.g. olaflur [(N.sup. 1-octadecyl-trimethylendiamine-N,N,N tris(2-ethanol)-2,2'-(3-n-(2-hydroxytheyl)octadecylamino]propyliminol)dihydro-floride] and dectaflur (9-octadecenylamine-hydrofluoride)), alexidine dihydrofluoride, hydrofluoride, ammonium fluoride, calcium fluoride, calcium carbonate monofluorophosphate, difluorosilane, fluoroaluminosilicate glass and any mixture thereof, hydrogen fluoride, fluoropolymer B (see U.S. Pat. No. 4,837,007), mixed salt neighborite (NaMgF3), magnesium fluoride, magnesium monofluorophosphate, potassium fluoride, lithium fluoride, indium fluoride, zirconium fluoride, copper fluoride, nickel fluoride, palladium fluoride, potassium fluorozirconate, tin fluorozirconate, sodium fluorozirconate, ammonium fluorozirconate, fluorosilicate fluorozirconate, fluoroborates, fluorozirconate, fluorostannites, fluorozirconate, sodium fluoride, stannous fluoride, stannous hexafluorozirconate, sodium hexafluorosilicate, sodium, lithium or potassium monofluorophosphate strontium fluoride and ytterbium trifluoride. Preferably, the active mineralisation agent is sodium fluoride, and/or hydrogen fluoride. This invention is not limited to the above but includes approaches such as the corporation of fluoride in the form of $Ca_5(PO_4)_3F$ (see U.S. Pat. No. 4,556,561). Variations in pH and salt types of fluorides (e.g. stannous, ammonium, titanium and amino fluorides) result in different retention of fluoride as calcium fluoride. For example, good results have been obtained using fluoride at lower pH values such as ammonium fluoride (see Jenkins, G. N. The Physiology and Biochemistry of the Mouth p. 495, 1978, Blackwell Scientific Publishing) and preferably thixotropic acidulated phosphate fluoride which can contain about 1-4% sodium fluoride with or without 0.1-0.8% hydrogen fluoride and 0.5-1.5% orthophosphoric acid (see Craig, R. G. et al Dental Materials, Properties and Manipulation p2-28, 2.sup.nd Ed 1979 CV Mosby Co.)

The period of fluoride exposure which causes significant rehardening of a demineralized enamel surface is about 4 hours (see Koulourides, T., Art and Science of Dental Caries Research pp. 355-378, 1968; Poole, D. F. G. and Silverstone, L. M., Hard tissue Growth Repair and Remineralisation, pp. 35-52, Ciba Fondation Symposium No. 11, Elsevier Scientific Publishing Company, 1973, Pearce E. I. F and Moore, A. J., J. Dent Res 64; 416-421, 1985). Obviously the period of fluoridation required is dependent on the type of material or device herein described, its fluoride type and concentration, frequency and period of delivery, other chemical or physical interventions (such as current and laser application) and the type of surface or lesion being treated. Furthermore, the effects can also be long term because of the deposition of pH controlled fluoride reservoirs of various $CaF_2$ forms.

The acute lethal dose of fluoride (F) is 33 mg F/Kg body weight and the chronic toxicity can be 0.1 mg F/Kg. Thus the determination of the fluoride concentration range is governed by the size and number of devices used or the volume of material used, the duration of applying the material or device, the rate of fluoride ion release and the weight of the patient. Thus the concentrations can range from about 7-0.2%. (See: A guide to the use of fluorides JADA 113:504-564, 1986, prepared by the National Fluoride Task force of the NFDH).

Mineralizing and/or Remineralizing Agents

Although fluoride is to date the most effective remineralization agent, this invention and practice thereof is not limited to fluoride alone but may include or be limited to any other mineralizing or remineralization agent known or to be developed or combination thereof. Examples are amorphous minerals, crystalline minerals and organic molecules.

An advantage of amorphous minerals is that they can be easy to mold into complex shapes (see Levi-Kalisman, Y. et al J. Chem. Soc. Dalton Trans 2000: 3977-3982, 2000) such as pits and fissures, demineralized enamel or dentin. These amorphous minerals can be present in stable or unstable phases. Silica (opal) is a stable type which can be formed by the polymineralization of silicic acid which can be mediated enzymatically. On the other hand amorphous calcium carbonate and amorphous calcium phosphate are unstable as they tend to transform into stable crystalline phases. Amorphous calcium phosphate, amorphous calcium phosphate fluoride, amorphous calcium carbonate phosphate, casein phosphopeptide, amorphous calcium phosphate nancomplexes, amorphous calcium carbonate phosphate fluoride, and amorphous calcium fluoride have high solubilities, fast formation rates and fast conversion rates to apatite (see U.S. Pat. No. 5,460,803). This transformation can be controlled, for example by mimicking chiton teeth where amorphous calcium phosphate is converted into dahllite. Besides these agents there are other agents such as dicalcium phosphate (in a dehydrate form or in an anhydrous form) which complement fluoride in remineralizing carious lesions (Wefel, J. S, and Harless, J. D. J. Dent Res 66: 1640-1643, 1987, Takagi, S. et al Caries Res 34: 281-288 (2000)).

Examples of crystalline minerals are aragonite, brushite (see U.S. Pat. Nos. 3,679,360 and 5,605,677), calcite, dahltite, ferrihydrite, fluoroapatite, hydroxyapatite (which can also be used in dissolved synthetic forms) or in a stannous hydroxyapatite fluoride (see U.S. Pat. No. 4,923,683), lepidocrocite, magnetite, octocalcium phosphate, vaterite and whitlockite. This invention also includes a system designed to alter a tooth surface thereby enhancing its resistance to caries and other pathology. For example the process of chiton radula formation can be fully or in part adapted to alter tooth surface clinically. For example iron atoms can be introduced which precipitate a hydrated iron-oxide mineral, ferrihydrite which can then be converted to magnetite or an iron oxide mineral, lepidocrocite. Another example is amorphous calcium phosphate which can be deposited and then induced to crystallize to dahllite or hydroxyapatite (see Addadi, L. and Weiner, S. Angew, Chem. Int. Ed. Engl. 31:15, 3-169, (1992). Besides hydroxyapatite, an often found mineral at remineralized or mineralize dental sites is whitlockite (Kodaka, T. et al Caries Res 26: 69-76 (1992). These amorphous or crystalline minerals can be used to restore demineralized tissue such as interproximal caries or to seal regions such as pits and fissures by chemical or physical intervention (such as laser application), to seal areas or alter the chemical surfaces thereof.

The organic material can be macromolecules such as acidic proteins, glycoproteins and sulfated polysaccharides (Addadi, L. and Weiner, S. Angew, Chem Int Ed Engl 31:153 169, (1992)) or smaller molecules such as polyaspartic and polyglutamic acid with or without a rigid substrate adsorption (Addadi, L. et al ACS Sym. Series no. 444, 1991).

Enhancing or Other Active Agents

These agents can be the matrix or part thereof or added to the matrix (e.g. silated hydroxyethylcellulose as apatite is formed because silanol chelates calcium (see Turezyn, R. et al J. Biomater Sci. Polym Ed 11:217, (2000)) polyampholyte-sodium fluoride and chlorhexidine (Wefel J. S. et al. Am J. Dent. 8, 217-220 (1995); Caufield, P. W. and Navia, J. M. in the Biological Basis of dental caries, Menaker, L. 406-407, Harper and Row, (1980), benzoate-like preserving agents (see Davis, B. A. et al Caries Res 35, 331-337, (2001), Isomalt® (Takatsuka, T. J. Dent Res. Sp Iss. A #2815 (2002), silanols (see Loty C et al J. Biomed. Mat. Res. 47; 367 (2000), and dicalcium phosphate dihydrate calcium carbonate (see U.S. Pat. No. 4,556,561 and Cury, J. A. et al Caries Res. 183 (2003). Calcium and phosphate are another example (ideally 1.5 m mol/L Ca and 0.9 m mol/L PO4) see Exterkate, R. A. M. et al J. Dent Res. 72 1599-1603 (1993). Examples of suitable calcium compounds are: calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium maleate, calcium maleate, calcium propionate calcium vaerate. Examples of suitable inorganic phosphates are alkali salts and ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate. Other active agents are (e.g. sodium lauryl sulphate (to reduce surface tension), azacycloheptane, diphosphonate, triclosan, polyvinyl methylether with maleic anhydride copolymer resins (see Zhang et al J. Clin. Dent 14: 23-28 (2003) xylitol, erythritol, vitamin E, aloe vera and rigid beta sheet proteins such as synthetic polyaspartate and polyglutamate proteins and natural agents purified from mineralized tissue such as glycoproteins phosphorylated amino acids and acidic sulfated polysaccharides (see Addadi et al ACS Symposium series 444; Addadi et al in Chemistry and Biology of Mineralized Tissues, Ed. Slavkin, H. and Price, P. Elsevier Sci. Pub. BV 153-162 (1992)), acidic macromolecules associated with hydrophobic macromolecules such as type I collagen, alpha and beta chiten (see Addadi, L. and Weiner, s. Angen. Chem. Int. Ed. Engl. 31: 153-169 (1992)) and other molecules and substances such as arginine, silk and elastin. They can also be inorganic agents such as zirconium and ferric pretreatments (see Clarkson B. H. et al. J. Dent. Res. 60:1912-1920 (1981) or organic solvents such as urea designed to clean the carious lesion (see Shellis, R. P. et al Eur. J. Oral Sci 110: 392-395, (2002), being part of the system described within the invention or they can be applied prior to the device application. Other agents can be commercial cocktails such as GC Tooth Mousse Recaldent™ or experimental cocktails such as synthetic enamel preparations.

Acidifying, Buffering or pH Regulating Agents

At least one agent can be included in the matrix or matrices to enhance fluoridation, mineralization or remineralization by altering the pH (3-7) (e.g. acidulated phosphate fluoride (derived from sodium fluoride acidulated with a mixture of sodium phosphate monobasic or dibasic, and phosphoric acid or from sodium fluoride, hydrogen fluoride and orthophosphoric acid), H.sub.3PO.sub.4, citric acid, sodium citrate, or sodium bicarbonate or by inducing buffering with for example calcium carbonate, arginine and polyacrylic acid fully neutralized with alkali metal ammonium or (alkylol) amine compound sodium polyacrylate (see U.S. Pat. No. 6,106,811). Furthermore, buffers may be required to enhance cross-linkage of the matrix or matrices (e.g. phosphate buffers at pH 6.8). Those knowledgeable in the art will know that more than one stage of buffering may be required prior to the production of the final product in order to facilitate required steps such as cross-linking or curing, and optimal pH of the final device which can be low 3-4 for optimal fluoridation remineralization or mineralization or neutral in order not to etch porcelain and tooth colored restorations. Agents which influence pH can also have important roles such as in the case of the remineralization of dentin which have been reported to only occur after the extraction.of proteins (see Clarkson, B. H. et al Caries Res 32: 357, 1998). Thus, the matrix or matrices could contain for example lactic acid, acetic acid, phosphoric acid or EDTA in a single matrix or on an external surface layer of a bi or multilayer device. On the other hand the dentin or enamel could be first primed with such agents using a liquid gel or an etching device, whereby the active agent is an acid, for example 37% phosphoric acid. Such a device could also be used to etch tooth surfaces prior to bonding of dental material. Another type of device could contain both the etching and bonding agent which is activated and/or cured, for example by water and/or light application (I.R., U.V. visual spectrum or lasers). One side of an interproximal device could be inactive and the second side could be an active site which could be used to fill, seal or coat interproximal sites, fissures, pits, lesions, caries, restoration defects or restoration-tooth margin defects. This second side could be a single phase or double phase system.

Another novel approach is the introduction of a buffering agent such as sodium bicarbonate during remineralization which penetrate into the subsurface lesion and then function as a buffering agent during acid challenges (see Tanaka, K. and Iijima, Y. J. of Dent. 29: 421-426 (2001)).

The Matrix and Cross-Linking Agents

The role of the matrix or matrices is to carry at least one primary active fluoridation mineralizing or remineralizing agent with or without at least one enhancing agent or other active agent and to provide the required viscosity, strength, plasticity and elasticity for application as well as the required stability or degradation pattern for the delivery of the active and any auxiliary agents, in order to provide the optimal rate and time span of ion or chemical interaction with the tooth surface and to provide a mobile environment for the appropriate ions and/or other chemicals to reach the tooth surface. Those knowledgeable and skilled in the art can alter the degradation by varying the concentrations and the degree of curing or cross-linking and type of cross-linking, or combinations thereof as well as the concentration and types of enzyme inhibitors, antimicrobial agents, preservatives and sterilizing agents which can interfere with intra-oral biodegradation. Some degradation properties may not be required in a matrix or part thereof if specific chemical or physical intervention requires instantaneous delivery.

The types of possible matrices are wide. They can include agents yet unused for dental treatment and agents such as those used as denture adhesives, impression materials, temporary, provisional or permanent restorations, sutures, perio- or surgical packs and periodontal agents (see Dental Therapeutics Digest Odontos Pub Inc.: Kay L. W. Drugs in Dentistry, Bristol 1972; O'Brien, W. J. and Ryge, G. An Outline of Dental Materials, Saunders 1978; Steinberg, D et al., J. Dent. Res. 67-208 Abstract No. 767, 1988; U.S. Pat. Nos. 5,324,519, 4,938,763, 5,278,201, 5,077,049, 5,739,176 and 5,733,950). The matrix or matrices material or materials may be sub-classified into natural products and synthetic products.

Polysaccharide polymers (e.g. agar, alginates, carboxymethylcellulose, carrageenan, cellulose, gellan gum, Kelcogel®, Kelcogel® F, Kelco Biopolymers, starches and retted flax extracts), lipids, polyisoprenes (e.g. latex rubber and gutta percha), resins and gums (e.g. tragacanth and storax) and proteins (e.g. alpha or beta chitin, soluble elastin and collagen or denatured collagen in the form of gelatin) are examples of natural products. In some cases agents may need to be treated, for example, dialyzed and de-ionized to remove impurities.

Purified collagen can be untreated or treated with fixing agents to prolong its resistance to digestion (similar to catgut surgical suture production). Denatured collagen can be impregnated with chromium salts to enhance its tensile strength and retard its absorption. A preferred polymeric matrix is a gelatin matrix, although those experienced in the art know the method of dissolution of gelatin is highly technique-sensitive and the method used can cause considerable differences in the texture. Further, gelatin, like collagen, can be lysine-cross linked with glutaraldehyde (an organelle preservant which has also been used for human aortic valve implants and dental pulp treatments; Kopel, H. M. et al., J. of Dent. for Child 47: 425-430, (1980)) and Periochip® Another possible cross-linking agent is formaldehyde, which forms intra- and intermolecular methylene bridges between various amino acids. Further examples include but are not limited to allyl methacrylate, 2,3- or 3,4-dehydroxybenzaldehyde, glycol dimethacrylate, nordihydroguaiacetic acid, rosemarinic acid, strontium, calcium, tannic acid and hexamethylenediisocyanate and chondroitin sulfate. Again, the biocompatibility of these agents must be carefully examined even though some of them have been used clinically. Physical means of treating gelatin to induce cross-linking are also possible for example by microwave-treatment (Vandelli, M. A. et al J. of Controlled Release 96, 67-84 (2004)). The gelatin may be of any source, for example bovine or non-mammalian gelatin. Bovine gelatin is preferably used when a matrix or matrices with higher rigidity is required.

It is prudent to note that a completely natural matrix of gelatin without cross-linking can also be used with an appropriate cover. Furthermore, natural cross-linkings are also feasible, for example calcium and hydroxylysin or leucine, dihydroxylysine or leucine (Traub W., and Piez, K., A. Adv. Protein Chem. 25:243-352, 1971), lysine, arginine, proteins, polysaccharides such as dextran, lipids such as sodium docusate and dehydrodihydroxylysine or leucine (Bailey, A. J. et al., Biochem. Biophys. Res. Commun. 35:663-671 (1969)), and enzymatic cross-linking, for example, by transglutaminase (Orban J. M. et al. J of Biomedical Materials Research 68A:756-762, (2004)).

Likely candidates within the boundary of possible synthetic products that may serve for the matrices of this invention are homopolymers or copolymers with a wide molecular weight range formed by condensation, additional anionic, cationic and/or catalytic polymerization systems. Examples are acrylamide based polymers and a cationic monomer (see U.S. Pat. No. 4,837,007) cyanoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly(methylmethacrylate) modified with small amounts of ethyl butyl or other alkyl methacrylates, polyethylene glycol, sodium polyacrylate PEG 400 and PEG 3350 and other carbomers. Some of these are indeed commercial or laboratory products such as polymethylvinylether-co-maleic anhydride and polyvinylether-co-maleic anhydride and polyvinyl pyrrolidone, carboxymethylcellulose, silated hydroxyethylcellulose or hydroxypropyl methylcellulose (Bourges et al Adv. In Colloid and Interface Sci 215-228: 2002; Bourges X. et al. Biopolymers 63:232-238: 2002) aqueous methacrylic polymer formulations for sustained and controlled release of dental and other products (e.g. Eudragit® Rohm). These polymers may require activators and cross-linking (see below). However, other agents are at times required, for example retarding agents such as hydroquinone and eugenol. Other yet different examples are zinc eugenolate, petrolateum and stearyl alcohol. Other gels may be included such as Carbopol polymers. (BF Goodrich Noveon) or a Na.sub.2Si O39H 2 0 solution mixed with phosphoric acid and hydrofluoric acid (see U.S. Pat. No. 3,679,360).

It is to be appreciated that the degree of cross-linking is of major significance to the rate of release of the active and/or auxiliary agents. The determination of the degree of cross-linking of the polymeric matrix or matrices is within the capabilities of the man of skill in the art of pharmacy. Other factors are antimicrobial agents, preservatives, sterilizing agents inhibitors (such as inhibitors of matrix metalloptoteinases (see WO 98/16503) and enzyme inhibitors which slow down the biodegradation of the matrix or matrices.

The matrices of the present invention can be strengthened not only by cross-linking, but also by other methods. For Example, U.S. Pat. No. 6,565,960 describes polymer composite compositions in which the polymer fibers, e.g. collagen fibers and gelatin, are strengthened by adding particular catechol-containing compounds, particularly compounds which have two or more catechol groups, to the polymeric material and forming a polymer of the compounds that intercalate within the polymeric material, e.g., forming a polymer composite. According to this U.S. patent, it is possible that the resulting polymer forms a scaffold-like structure throughout the polymeric material without the necessity of cross-linking the individual polymeric materials, e.g., collagen or gelatin polypeptides. This scaffolding provides synthetic polymer fibers having a tensile strength, stiffness, and strain at failure that is comparable to or better than natural polymeric material fibers. As all references cited herein, also U.S. Pat. No. 6,565,960 is fully herein incorporated.

Other novel matrices which can also be used as matrix and sealing agents, for example at pit and fissures, are Sn—Sn catenation, Sn—Cl chains or lattices or Sn protein chains (see Jodaikin, A. and Goldstein, S., J. Dent. 16:140-144, (1988)), and even combinations with fluoride, calcium, phosphate and tin (see Harris, N. O. and Christen, A. G. Primary Preventive Dentistry 4.sup.th Ed Norwalk Appleton Longe 1995; Wu. H. et al, abstract from Hua Zi Kou Qiang Yi Xue Za Zhi 18: 219-221, (2000)).

Yet another novelty is a matrix or matrices which is or includes a matrix-bound fluoride ion exchange system which can be 'recharged' with fluoride from external sources such as toothpastes, oral rinses, dental materials (see U.S. Pat. No. 5,639,840) and professionally applied fluoride systems (see Zimmerman, B. F. et al J. Dent. Res. 63:689-692 (1984); Fuji 1.times.GP® fast by GC Inc.).

Although the matrix or matrices are defined as a delivery system, this invention does not preclude the use of the matrix or matrices itself as a template or framework to control remineralization or mineralization based on control and design principles culled from biological mineralization or fabricated synthetic analogs.

Preservatives and Sterilizing Agents

The addition of preservatives and sterilizing agents may be advantageous particularly for long-dwelling matrices, as they will inhibit the development of various microorganisms such as bacteria, fungi and yeast, and they could play a role in inhibiting the biodegradation of the matrix or matrices, thereby influencing its longevity and the release of the active agent. Examples of preservatives are benzoic acid, biguanide, polyamino propyl biguanide, cetyl pyridinium chloride, phenol, methylparaben, metal proteins (see Horman, H. in Sigel, H. Metal Ions in Biological Systems Vol 3 New York Marcel and Dekker pg 105, 1974 and Jodaikin, A. and Goldstein, S. J. Dent 16:140-144, (1988)), and sodium bicarbonate, sorbic acid, thymol and examples of sterilizing agents are iodine, potassium and alcohol.

Stabilizing Agents

The purpose is to inhibit an unwanted or premature reaction such as reactions of calcium phosphate and fluoride by chemical means or physical means such as the use of a varnishing, coating or encapsulation agent.

Antimicrobial Agents

Included agents for therapeutic functions can be antibacterial, antiviral, antifungal and other antimicrobial agents. Indeed stannous fluoride has shown antibacterial activity (see Paine, M. L. et al JADA 129, 6977, (1998)). Other examples are alexidine, chlorhexidine digluconate, hexetidine, copper zinc citrate and stannous pyrophosphate, triclosan, cetylpyridinium chloride and halogenated bisphenolec compounds.

Cleaning Agents

The invention can function as an interproximal site cleaning system as an alternative or supplement to flossing. The invention would thus need to include agents such as a surfactant or sudsing agent which foam throughout a wide pH range. Examples of cleaning agents are sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium lauryl carboxylate, sodium dodecyl benzenesulfonate, poloxamers, polyoxyethylene sorbitan esters, fatty alcohol ethoxylates, polyethylene oxide, cocamidoppropyl betaine, hydrogen peroxide, sodium bicarbonate, monosodiumphosphate, sodium hydroxide, potassium hydroxide, sodium carbonate and imidazole. Another possibility is effervescing agents of systems such as the use of a sodium bicarbonate/citric acid system. The effervescing loosens or dislodges interproximal plaque and debris at a microscopic level thereby overcoming flossing which cannot negotiate rough surfaces, especially at the microscopic level.

Tooth Desensitizing Agents

Examples are fluorides (see above), potassium citrate, potassium chloride, potassium tartrate, potassium bicarbonate, potassium oxalate and potassium nitrate.

Whitening or Bleaching Agents

Although Whitestrips® by Crest have been marketed as a tooth whitening system in the form of a strip which contains hydrogen peroxide this invention includes a system to whiten difficult areas to access such as interproximal regions. The agents that can be used include hydrogen peroxide, carbamide peroxide, metal chlorites such as calcium chlorite, barium chlorite, magnesium chlorite, lithium chlorite, sodium chlorite, potassium chlorite, hypochlorite, perborates, percarbonates, peroxy acids, persulfates, urea peroxide, calcium peroxide, chlorine dioxide, sodium percarbonate, oxones, and even enzymes such as protease (see U.S. Pat. No. 6,521,215). Stabilizing agents may also be required, for example dipicolinic acid or sodium stannate for peroxy bleaching agents.

Gingiva and Periodontal Agents:

Agents listed in any of the above categories, antimicrobial and cleaning agents can be included, especially chlorhexidine digluconate and hydrogen peroxide (the latter can be combined with baking powder). Other examples are hyaluronic acid, thymol, doxycycline, and tetracycline hydrochloride.

Anticalculus Agents

Examples are alkalimetal pyrophosphates, hypophosphite-containing polymers, organic phosphonates, and phosphocitrates. Indeed some anti-calculus agents could enhance anticaries activity and improve fluoride availability (see Zhang, Y. P. et al J. Clin. Dent 14: 23-28, (2003)).

Hemostatic Agents

This category includes vasoconstrictors (e.g. adrenalin), absorbable agents (e.g. oxidised cellulose, fibrin, calcium alginate), thromboplastic agents (e.g. thrombin), chemical agents (e.g. aluminum chloride, tannic acid, ferric chloride, ferric sulphate zinc chloride, alum, hyaluronic acid hydrogen peroxide) or physical plugging (e.g. the device includes bone wax). The role of a hemostat would be to stop bleeding which could hamper fluoridation or chemical treatment in regions where bleeding is caused by gingival or other bleeding.

Liquid Vehicles

Liquid vehicles may be solvents used particularly when preparing the matrix or matrices or to facilitate application. Examples are water, polydimethylsiloxane, ethyl alcohol or glycerin (glycerol) alone or in any combination.

Plasticisers and Elasticisers

Plasticisers and elasticisers may be used to modify the mechanical properties of the matrix or matrices, where needed and desired. Examples are polyethylene glycol, dibutyl phthalate, glycerol, sorbitol, mineral salts, olive oil, linseed oil, light mineral oil, polymers of ethylene propylene, polyolefins, polyacrylates polymethylates, styrene-butadiene, vinyl ethylene acetate copolymers, butadiene isoprene, gum base, silicone resins and gums, silk and elastin for example, purified from a natural rubbery protein from Ligamentum nuchae.

Another example is carboxypolymethylene which can also be incorporated in the matrix or matrices in order to increase the viscosity of the device and reduce the sorption of saliva thereby also influencing the biodegradation of the device.

According to some embodiments of present invention, the matrix or matrices may be made from any suitable material as described above, such as for example gelatin, in combination with an elasticiser, such as for example soluble elastin, sorbitol or gum base, the gelatin being preferably cross-linked and bound to soluble elastin using any suitable material such as for example glutaraldehyde, nordihydroguaiaretic acid and/or tannic acid. Such matrices have adequate plastic properties and are at the same time of sufficient toughness to maintain the mechanical integrity of the system when affixed at a dental site.

Adhering Agents

Agents may be added to facilitate adhesion to dental surface.

Examples are white wax, bees wax, rosin (colophonium bases), shellac, gum mastic and polybutene.

Fillers, Softeners and Binders

The matrix or matrices may also comprise fillers and/or softeners and/or binders such as beeswax, coconut oil, corn syrup, gum Arabic, gum mastic, flour, hydrogenated castor oil, kaolin (aluminum silicate), magnesium oxide, paraffin, silicon dioxide, sodium carboxymethyl-cellulose, xanthan gum, zinc oxide or other various inorganic molecules. It should be noted that certain ions may inhibit remineralization in some cases (for example $P_{20}_7$, $HCO_3$, $SiO_4$, $CrO_4$, Mg and Zn) and some inorganic fillers can be coated with water repellant coupling agents such as vinyl silane. Examples of softeners are lecithin and waxes.

Coloring or Staining Agents

These include agents to enhance the appearance of the applied at least one matrix, and dyes which are released to enhance caries detection, as discussed above. Examples are fuchsin or acid red 52 in propylene glycol. These diagnostic dyes include conventional histological stains, clinical decay detection agents and agents whose detection can be enhanced with light, for example fluorescence agents by UV light or other agents activated by intense light within the visual spectrum, or agents drawn by blotting of the lesion after the device or material is removed and the tooth surface rinsed. A color change system could also be used to indicate for example stages of degradation of the device, pH of the site and/or amounts of fluoride at the site. Another application of coloring is the need for marking of the surface to be treated with a dye in the said device which enhances the effects of lasers such as Nd.Yag (Neodymium-Yttrium Aluminum-Garnet lasers, see Miller, M, and Truhe, T. JADA 124:32 (1993)).

Flavoring or Sweetening Agents and Breath Fresheners or Sensates (Warming or Cooling Agents)

A flavoring or sweetening or sensate agent may be added to the matrix or matrices, for example, menthol, sodium saccharin, sorbitol, aspartame, sodium chloride. Also breath fresheners may be added to the matrix or matrices, for example parsley seed, methyl salicylate, sunflower oils and peppermint oil.

It is understood that the invention can include a thickening agent, a sudsing agent, a dessicating agent, an anti-plaque agent, an anti-inflammatory agent, humectants, nutrients, an analgesic or anesthetic agent, antioxidants or another therapeutic or cosmetic agent or mixtures thereof for oral and systemic use/uses.

The matrix or matrices is preferably made from a material, such as for example gelatin cross-linked by glutaraldehyde, nordihydroguaiaretic acid and/or tannic acid that is resorbable and/or biodegradable in the saliva by host enzymes, bacteria or by means of the dissolution properties of the saliva or drinks. Nonetheless, the matrix or matrices may alternatively be made from a non-resorbable material which also releases the active material or materials that is being delivered to the target area. For example, the matrix or matrices may be made from rubber latex, a polymer or any one of a large variety of sugars, lipids, nucleic acids or other proteins found in rubber latex bonded to an amine fluoride which is released in the mouth because of, for example, a host enzyme.

According to another aspect of the invention there is provided a device for the removal of a material or materials having a predetermined intra-oral activity from dental surfaces of the oral cavity, typically tooth surfaces or gums, and in particular from interproximal sites or furcations, the device comprising a matrix or matrices that is configured for absorbing said material or materials, for example from the saliva or from an adjacent material (for example gels or varnishes). Alternatively, such matrix can be used for placing other materials on at least one of the surfaces of the device prior to placement (for example varnishes, gels, liquids, cements or other dental materials or agents). For example, such a matrix can be similar to other matrices as disclosed herein (for example see above "The Matrix and Cross-Linking Agents"), mutatis mutandis, but carry no active agent. For example, the respective matrix is configured for obtaining calcium and phosporous from the saliva, or elements such as fluorine from a varnish cement or gel placed on or adjacent to the matrix outside of or inside the mouth of the patient.

The matrices and devices of this invention and the manufacture thereof are not limited to the above chemical components, but encompass all their variations, and include other chemicals as only examples have been presented above. Further, the biocompatibility of these agents and their interactions need to be carefully examined and tested prior to clinical application.

While examples of the invention have been described by way of illustration, it will be apparent that the invention can be carried into practice with many modifications, variations and adaptations, and with the use of numerous equivalents or alternative solutions that are within the scope of persons skilled in the art, without exceeding the scope of the claims.

The invention claimed is:

1. A substrate having a substrate width dimension, a substrate length dimension and a substrate thickness dimension, the substrate made from a polymeric matrix material and capable of containing at least one active material having a predetermined intraoral activity or at least one inactive material, wherein at least one of said substrate width dimension or said substrate length dimension is sufficiently large to enable at least two precursor portions of the substrate to be separated from the substrate, each precursor portion being manipulable to enable altering at least one of the shape and size of the precursor portion to thereby provide a retention device that is configured for being retained at a dental site and for delivering the active material or inactive material to a dental site, said substrate further comprising a plurality of separating facilitators defining separation boundaries between said precursor portions and configured for facilitating separation of respective said precursor portions from a remainder of said substrate;
 wherein said retention device is one of: substantially biodegradable, self-degradable, substantially resorbable and substantially non-resorbable, and
 further comprising stiffening elements embedded in the matrix material;
 wherein said stiffening elements comprise a plurality of fibers;
 wherein each said precursor portion is foldable about a fold line to thereby provide said retention device; and
 wherein said fibers are arranged such as not to cross said fold line.

2. The substrate according to claim 1, wherein said separating facilitator includes one of the group consisting of the following:
 at least one first weakened line configured for facilitating separation of each said precursor portion from an adjoining precursor portion
 at least one first weakened line configured for facilitating separation of each said precursor portion from an adjoining precursor portion via a respective connector portion therebetween
 an indented line;
 a perforated line;
 a physical indicating mark along a separation line; and
 a chemically treated indicating mark along a separation line.

3. The substrate according to claim 1, wherein each said precursor portion is trimmable to thereby provide the retention device.

4. The substrate according to claim 1, wherein said retention device is soft for easy interproximal insertion, and provides a cleaning effect which would serve as an alternative or supplement to flossing and releases at least one antimicrobial or cleansing agent and/or at least one remineralizing or mineralizing agent, and/or at least one demineralization inhibiting agent.

5. The substrate according to claim 1, wherein the polymeric matrix material comprises a hydrophilic polymer such as to enable the respective said retention device to be affixed by swelling in situ by the hydration of the respective matrix in the oral cavity after accommodation of said retention device at the dental site.

6. The substrate according to claim 1, wherein said fibers are arranged in generally parallel relationship with the fold line of the respective said precursor portion.

7. The substrate according to claim 1, wherein said fibers are at an angle of up to ±45° to the fold line.

8. The substrate according to claim 1, wherein said fibers are arranged randomly aligned in the matrix.

9. The substrate according to claim 1, wherein said fibers are arranged aligned in two or more parallel groups to form various ordered mesh-like alignments.

10. The substrate according to claim 9, wherein said mesh-like alignments can be uniform or restricted to specific areas with respect to the matrix or its precursor portion.

11. The substrate according to claim 9, wherein said fibers include one or more of or made from any one of or combination of: glass fibers, carbon fibers, natural silk fibers, silicon carbide and nitride, boron, alumina ($Al_2O_3$), synthetic polymers, and tin chains.

12. The substrate according to claim 1, wherein said fibers are one of bound to the matrix or unbound within the matrix.

13. A substrate having a substrate width dimension, a substrate length dimension and a substrate thickness dimension, the substrate made from a polymeric matrix material and containing at least one active material having a predetermined intraoral activity or at least one inactive material, wherein at least one of said substrate width dimension or said substrate length dimension is sufficiently large to enable at least two precursor portions of the substrate to be separated from the substrate, each precursor portion being manipulable to enable altering at least one of the shape and size of the precursor portion to thereby provide a retention device that is configured for being retained at a dental site and for delivering the active material or inactive material to a dental site, said substrate further comprising a plurality of separating facilitators defining separation boundaries between said precursor portions and configured for facilitating separation of respective said precursor portions from a remainder of said substrate;
 wherein said retention device is one of: substantially biodegradable, self-degradable, substantially resorbable and substantially non-resorbable, and
 further comprising stiffening elements embedded in the matrix material;
 wherein said stiffening elements comprise a plurality of fibers;
 wherein each said precursor portion is foldable about a fold line to thereby provide said retention device; and
 wherein said fibers are arranged such as not to cross said fold line.

14. The substrate according to claim 13, wherein the polymeric matrix material comprises a hydrophilic polymer that enables the respective said retention device to be affixed by swelling in situ by the hydration of the respective matrix in the oral cavity after accommodation of said retention device at the dental site.

15. The substrate according to claim 13, wherein the matrix material further comprises any one of an enhancing agent for enhancing the application and release of the active material such as plasticizer, elasticizer, coloring agents, adhering agent, filler, softener, binder and preserving or sterilizing agent or any one of an auxiliary agent such as an antimicrobial agent, anti plaque agent, anti inflammatory agent, antioxidant, humectants, nutrient analgesic or anaesthetic agent, anti calculus agent, cleaning agent, effervescent agent, tooth desensitizing agent, staining agent, hemostatic agent, astringent agent, whitening or bleaching agent, flavoring or sweetening agent, breath freshener, or sensate.

16. The substrate according to claim 13, wherein the active material is at least one of a fluoridation agent, a antimicrobial agent, a remineralization agent, a mineralization agent, a demineralization inhibiting agent, a cleaning agent, a tooth desensitizing agent and a tooth whitening/bleaching agent.

* * * * *